US012779120B2

(12) United States Patent
Hayter et al.

(10) Patent No.: US 12,779,120 B2
(45) Date of Patent: Nov. 3, 2026

(54) CLOSED LOOP CONTROL AND SIGNAL ATTENUATION DETECTION

(71) Applicant: Abbott Diabetes Care Inc., Alameda, CA (US)

(72) Inventors: Gary Hayter, Oakland, CA (US); Erwin S. Budiman, Fremont, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 703 days.

(21) Appl. No.: 18/310,980

(22) Filed: May 2, 2023

(65) Prior Publication Data

US 2023/0263955 A1 Aug. 24, 2023

Related U.S. Application Data

(63) Continuation of application No. 16/252,973, filed on Jan. 21, 2019, now Pat. No. 11,679,200, which is a (Continued)

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/14546* (2013.01); (Continued)

(58) Field of Classification Search
CPC ................ A61M 5/1723; A61M 5/142; A61M 2205/18; A61M 2205/3303; (Continued)

(56) References Cited

U.S. PATENT DOCUMENTS 3,581,062 A 5/1971 Aston
3,926,760 A 12/1975 Allen et al.
(Continued)

FOREIGN PATENT DOCUMENTS

EP 0098592 A2 1/1984
EP 0320109 A1 6/1989
(Continued)

OTHER PUBLICATIONS

STS-7 Continuous Glucose Monitoring System User's Guide, 74 pages; 2007; Anlage TW 11 D5a, Taylor Wessing, Statement of Defence in *Abbott* v. *Dexcom*, Opposition to EP 3782539.
(Continued)

*Primary Examiner* — Cris L. Rodriguez
(74) *Attorney, Agent, or Firm* — Sterne, Kessler, Goldstein & Fox P.L.L.C.

(57) ABSTRACT

Methods, system and devices for monitoring a plurality of parameters associated with a closed loop control operation including continuously monitoring a physiological condition and automatic administration of a medication, detecting a signal level associated with the monitored physiological condition deviating from a predetermined threshold level, retrieving the medication level administered associated with a time period of the detected signal level, applying the retrieved medication level to the detected signal based on a predefined predictive model to generate a predictive signal, and comparing the detected signal to the predictive signal to determine whether a condition associated with the detected signal level is present are provided.

20 Claims, 12 Drawing Sheets

100

Related U.S. Application Data continuation of application No. 15/184,961, filed on Jun. 16, 2016, now Pat. No. 10,188,794, which is a continuation of application No. 12/202,304, filed on Aug. 31, 2008, now Pat. No. 9,392,969.

(51) Int. Cl.

| | |
|---|---|
| ***A61B 5/145*** | (2006.01) |
| ***A61B 5/1495*** | (2006.01) |
| ***A61M 5/142*** | (2006.01) |
| ***G16H 20/17*** | (2018.01) |

(52) U.S. Cl.

CPC ........... *A61B 5/4839* (2013.01); *A61M 5/142* (2013.01); *G16H 20/17* (2018.01); *A61B 5/0031* (2013.01); *A61B 5/1495* (2013.01); *A61M 2205/18* (2013.01); *A61M 2205/3303* (2013.01); *A61M 2205/3507* (2013.01); *A61M 2205/50* (2013.01); *A61M 2205/581* (2013.01); *A61M 2205/582* (2013.01); *A61M 2205/583* (2013.01); *A61M 2205/702* (2013.01); *A61M 2230/201* (2013.01)

(58) Field of Classification Search

CPC ...... A61M 2205/3507; A61M 2205/50; A61M 2205/581; A61M 2205/582; A61M 2205/583; A61M 2205/702; G16H 20/17; A61B 5/14532; A61B 5/14546; A61B 5/4839; A61B 5/0031; A61B 5/1495

See application file for complete search history.

(56) References Cited

U.S. PATENT DOCUMENTS

| | | | |
|---|---|---|---|
| 3,949,388 | A | 4/1976 | Fuller |
| 3,960,497 | A | 6/1976 | Acord |
| 3,978,856 | A | 9/1976 | Michel |
| 4,036,749 | A | 7/1977 | Anderson |
| 4,055,175 | A | 10/1977 | Clemens et al. |
| 4,129,128 | A | 12/1978 | McFarlane |
| 4,245,634 | A | 1/1981 | Albisser et al. |
| 4,327,725 | A | 5/1982 | Cortese et al. |
| 4,344,438 | A | 8/1982 | Schultz |
| 4,349,728 | A | 9/1982 | Phillips et al. |
| 4,373,527 | A | 2/1983 | Fischell |
| 4,392,849 | A | 7/1983 | Petre et al. |
| 4,425,920 | A | 1/1984 | Bourland et al. |
| 4,431,004 | A | 2/1984 | Bessman et al. |
| 4,441,968 | A | 4/1984 | Emmer et al. |
| 4,462,048 | A | 7/1984 | Ross |
| 4,464,170 | A | 8/1984 | Clemens et al. |
| 4,478,976 | A | 10/1984 | Goertz et al. |
| 4,494,950 | A | 1/1985 | Fischell |
| 4,509,531 | A | 4/1985 | Ward |
| 4,527,240 | A | 7/1985 | Kvitash |
| 4,538,616 | A | 9/1985 | Rogoff |
| 4,545,382 | A | 10/1985 | Higgins et al. |
| 4,619,793 | A | 10/1986 | Lee |
| 4,671,288 | A | 6/1987 | Gough |
| 4,703,756 | A | 11/1987 | Gough et al. |
| 4,711,245 | A | 12/1987 | Higgins et al. |
| 4,731,051 | A | 3/1988 | Fischell |
| 4,731,726 | A | 3/1988 | Allen, III |
| 4,749,985 | A | 6/1988 | Corsberg |
| 4,757,022 | A | 7/1988 | Shults et al. |
| 4,759,366 | A | 7/1988 | Callaghan |
| 4,777,953 | A | 10/1988 | Ash et al. |
| 4,779,618 | A | 10/1988 | Mund et al. |
| 4,847,785 | A | 7/1989 | Stephens |
| 4,854,322 | A | 8/1989 | Ash et al. |
| 4,871,351 | A | 10/1989 | Feingold |
| 4,890,620 | A | 1/1990 | Gough |
| 4,925,268 | A | 5/1990 | Iyer et al. |
| 4,947,845 | A | 8/1990 | Davis |
| 4,953,552 | A | 9/1990 | DeMarzo |
| 4,986,271 | A | 1/1991 | Wilkins |
| 4,995,402 | A | 2/1991 | Smith et al. |
| 5,000,180 | A | 3/1991 | Kuypers et al. |
| 5,002,054 | A | 3/1991 | Ash et al. |
| 5,019,974 | A | 5/1991 | Beckers |
| 5,050,612 | A | 9/1991 | Matsumura |
| 5,051,688 | A | 9/1991 | Murase et al. |
| 5,055,171 | A | 10/1991 | Peck |
| 5,068,536 | A | 11/1991 | Rosenthal |
| 5,077,476 | A | 12/1991 | Rosenthal |
| 5,082,550 | A | 1/1992 | Rishpon et al. |
| 5,106,365 | A | 4/1992 | Hernandez |
| 5,113,869 | A | 5/1992 | Nappholz et al. |
| 5,122,925 | A | 6/1992 | Inpyn |
| 5,135,004 | A | 8/1992 | Adams et al. |
| 5,148,812 | A | 9/1992 | Verrier et al. |
| 5,165,407 | A | 11/1992 | Wilson et al. |
| 5,199,428 | A | 4/1993 | Obel et al. |
| 5,202,261 | A | 4/1993 | Musho et al. |
| 5,203,326 | A | 4/1993 | Collins |
| 5,204,264 | A | 4/1993 | Kaminer |
| 5,210,778 | A | 5/1993 | Massart |
| 5,228,449 | A | 7/1993 | Christ et al. |
| 5,231,988 | A | 8/1993 | Wernicke et al. |
| 5,246,867 | A | 9/1993 | Lakowicz et al. |
| 5,251,126 | A | 10/1993 | Kahn et al. |
| 5,262,035 | A | 11/1993 | Gregg et al. |
| 5,262,305 | A | 11/1993 | Heller et al. |
| 5,264,104 | A | 11/1993 | Gregg et al. |
| 5,264,105 | A | 11/1993 | Gregg et al. |
| 5,279,294 | A | 1/1994 | Anderson et al. |
| 5,284,425 | A | 2/1994 | Holtermann et al. |
| 5,285,792 | A | 2/1994 | Sjoquist et al. |
| 5,293,877 | A | 3/1994 | O'Hara et al. |
| 5,299,571 | A | 4/1994 | Mastrototaro |
| 5,313,953 | A | 5/1994 | Yomtov et al. |
| 5,320,715 | A | 6/1994 | Berg |
| 5,320,725 | A | 6/1994 | Gregg et al. |
| 5,322,063 | A | 6/1994 | Allen et al. |
| 5,328,460 | A | 7/1994 | Lord et al. |
| 5,330,634 | A | 7/1994 | Wong et al. |
| 5,340,722 | A | 8/1994 | Wolfbeis et al. |
| 5,342,789 | A | 8/1994 | Chick et al. |
| 5,356,786 | A | 10/1994 | Heller et al. |
| 5,360,404 | A | 11/1994 | Novacek et al. |
| 5,365,426 | A | 11/1994 | Siegel et al. |
| 5,372,427 | A | 12/1994 | Padovani et al. |
| 5,376,070 | A | 12/1994 | Purvis et al. |
| 5,379,238 | A | 1/1995 | Stark |
| 5,384,547 | A | 1/1995 | Lynk, Jr. et al. |
| 5,390,671 | A | 2/1995 | Lord et al. |
| 5,391,250 | A | 2/1995 | Cheney, II et al. |
| 5,400,795 | A | 3/1995 | Murphy et al. |
| 5,408,999 | A | 4/1995 | Singh et al. |
| 5,410,326 | A | 4/1995 | Goldstein |
| 5,411,647 | A | 5/1995 | Johnson et al. |
| 5,425,749 | A | 6/1995 | Adams |
| 5,425,868 | A | 6/1995 | Pedersen |
| 5,429,602 | A | 7/1995 | Hauser |
| 5,431,160 | A | 7/1995 | Wilkins |
| 5,431,921 | A | 7/1995 | Thombre |
| 5,438,983 | A | 8/1995 | Falcone |
| 5,462,645 | A | 10/1995 | Albery et al. |
| 5,472,317 | A | 12/1995 | Field et al. |
| 5,489,414 | A | 2/1996 | Schreiber et al. |
| 5,497,772 | A | 3/1996 | Schulman et al. |
| 5,505,828 | A | 4/1996 | Wong et al. |
| 5,507,288 | A | 4/1996 | Bocker et al. |
| 5,509,410 | A | 4/1996 | Hill et al. |
| 5,514,718 | A | 5/1996 | Lewis et al. |
| 5,520,191 | A | 5/1996 | Karlsson et al. |
| 5,531,878 | A | 7/1996 | Vadgama et al. |
| 5,532,686 | A | 7/1996 | Urbas et al. |
| 5,543,326 | A | 8/1996 | Heller et al. |
| 5,552,997 | A | 9/1996 | Massart |
| 5,568,400 | A | 10/1996 | Stark et al. |
| 5,568,806 | A | 10/1996 | Cheney, II et al. |

(56) References Cited

U.S. PATENT DOCUMENTS

| | | | |
|---|---|---|---|
| 5,569,186 | A | 10/1996 | Lord et al. |
| 5,582,184 | A | 12/1996 | Erickson et al. |
| 5,586,553 | A | 12/1996 | Halili et al. |
| 5,593,852 | A | 1/1997 | Heller et al. |
| 5,601,435 | A | 2/1997 | Quy |
| 5,609,575 | A | 3/1997 | Larson et al. |
| 5,628,310 | A | 5/1997 | Rao et al. |
| 5,628,324 | A | 5/1997 | Sarbach |
| 5,628,890 | A | 5/1997 | Carter et al. |
| 5,634,468 | A | 6/1997 | Platt et al. |
| 5,640,954 | A | 6/1997 | Pfeiffer et al. |
| 5,653,239 | A | 8/1997 | Pompei et al. |
| 5,660,163 | A | 8/1997 | Schulman et al. |
| 5,665,065 | A | 9/1997 | Colman et al. |
| 5,665,222 | A | 9/1997 | Heller et al. |
| 5,707,502 | A | 1/1998 | McCaffrey et al. |
| 5,711,001 | A | 1/1998 | Bussan et al. |
| 5,711,861 | A | 1/1998 | Ward et al. |
| 5,720,295 | A | 2/1998 | Greenhut et al. |
| 5,724,030 | A | 3/1998 | Urbas et al. |
| 5,726,646 | A | 3/1998 | Bane et al. |
| 5,733,259 | A | 3/1998 | Valcke et al. |
| 5,735,285 | A | 4/1998 | Albert et al. |
| 5,738,220 | A | 4/1998 | Geszler |
| 5,741,211 | A | 4/1998 | Renirie et al. |
| 5,748,103 | A | 5/1998 | Flach et al. |
| 5,749,907 | A | 5/1998 | Mann |
| 5,771,891 | A | 6/1998 | Gozani |
| 5,772,586 | A | 6/1998 | Heinonen et al. |
| 5,785,660 | A | 7/1998 | van Lake et al. |
| 5,791,344 | A | 8/1998 | Schulman et al. |
| 5,792,065 | A | 8/1998 | Xue et al. |
| 5,804,047 | A | 9/1998 | Karube et al. |
| 5,820,551 | A | 10/1998 | Hill et al. |
| 5,822,715 | A | 10/1998 | Worthington et al. |
| 5,833,603 | A | 11/1998 | Kovacs et al. |
| 5,842,189 | A | 11/1998 | Keeler et al. |
| 5,891,047 | A | 4/1999 | Lander et al. |
| 5,891,049 | A | 4/1999 | Cyrus et al. |
| 5,899,855 | A | 5/1999 | Brown |
| 5,914,026 | A | 6/1999 | Blubaugh, Jr. et al. |
| 5,918,603 | A | 7/1999 | Brown |
| 5,925,021 | A | 7/1999 | Castellano et al. |
| 5,935,224 | A | 8/1999 | Svancarek et al. |
| 5,942,979 | A | 8/1999 | Luppino |
| 5,951,485 | A | 9/1999 | Cyrus et al. |
| 5,957,854 | A | 9/1999 | Besson et al. |
| 5,960,797 | A | 10/1999 | Kramer et al. |
| 5,961,451 | A | 10/1999 | Reber et al. |
| 5,964,993 | A | 10/1999 | Blubaugh, Jr. et al. |
| 5,965,380 | A | 10/1999 | Heller et al. |
| 5,971,922 | A | 10/1999 | Arita et al. |
| 5,972,199 | A | 10/1999 | Heller et al. |
| 5,980,708 | A | 11/1999 | Champagne et al. |
| 5,995,860 | A | 11/1999 | Sun et al. |
| 6,001,067 | A | 12/1999 | Shults et al. |
| 6,016,443 | A | 1/2000 | Ekwall et al. |
| 6,021,350 | A | 2/2000 | Mathson |
| 6,024,699 | A | 2/2000 | Surwit et al. |
| 6,028,413 | A | 2/2000 | Brockmann |
| 6,038,469 | A | 3/2000 | Karlsson et al. |
| 6,049,727 | A | 4/2000 | Crothall |
| 6,052,565 | A | 4/2000 | Ishikura et al. |
| 6,066,243 | A | 5/2000 | Anderson et al. |
| 6,071,391 | A | 6/2000 | Gotoh et al. |
| 6,073,031 | A | 6/2000 | Helstab et al. |
| 6,083,710 | A | 7/2000 | Heller et al. |
| 6,088,608 | A | 7/2000 | Schulman et al. |
| 6,091,976 | A | 7/2000 | Pfeiffer et al. |
| 6,091,987 | A | 7/2000 | Thompson |
| 6,093,172 | A | 7/2000 | Funderburk et al. |
| 6,096,364 | A | 8/2000 | Bok et al. |
| 6,103,033 | A | 8/2000 | Say et al. |
| 6,108,577 | A | 8/2000 | Benser |
| 6,112,116 | A | 8/2000 | Fischell et al. |
| 6,115,628 | A | 9/2000 | Stadler et al. |
| 6,117,290 | A | 9/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,121,611 | A | 9/2000 | Lindsay et al. |
| 6,122,351 | A | 9/2000 | Schlueter, Jr. et al. |
| 6,128,526 | A | 10/2000 | Stadler et al. |
| 6,130,623 | A | 10/2000 | MacLellan et al. |
| 6,134,461 | A | 10/2000 | Say et al. |
| 6,143,164 | A | 11/2000 | Heller et al. |
| 6,144,837 | A | 11/2000 | Quy |
| 6,144,871 | A | 11/2000 | Saito et al. |
| 6,159,147 | A | 12/2000 | Lichter et al. |
| 6,161,095 | A | 12/2000 | Brown |
| 6,162,611 | A | 12/2000 | Heller et al. |
| 6,175,752 | B1 * | 1/2001 | Say .......................... A61B 5/01 128/903 |
| 6,200,265 | B1 | 3/2001 | Walsh et al. |
| 6,212,416 | B1 | 4/2001 | Ward et al. |
| 6,219,574 | B1 | 4/2001 | Cormier et al. |
| 6,233,471 | B1 | 5/2001 | Berner et al. |
| 6,233,486 | B1 | 5/2001 | Ekwall et al. |
| 6,248,067 | B1 | 6/2001 | Causey, III et al. |
| 6,249,705 | B1 | 6/2001 | Snell |
| 6,254,586 | B1 | 7/2001 | Mann et al. |
| 6,256,538 | B1 | 7/2001 | Ekwall |
| 6,264,606 | B1 | 7/2001 | Ekwall et al. |
| 6,270,455 | B1 | 8/2001 | Brown |
| 6,272,379 | B1 | 8/2001 | Fischell et al. |
| 6,275,717 | B1 | 8/2001 | Gross et al. |
| 6,283,761 | B1 | 9/2001 | Joao |
| 6,284,478 | B1 | 9/2001 | Heller et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,296,571 | B1 | 10/2001 | McVicar |
| 6,299,347 | B1 | 10/2001 | Pompei |
| 6,299,757 | B1 | 10/2001 | Feldman et al. |
| 6,306,104 | B1 | 10/2001 | Cunningham et al. |
| 6,309,884 | B1 | 10/2001 | Cooper et al. |
| 6,314,317 | B1 | 11/2001 | Willis |
| 6,329,161 | B1 | 12/2001 | Heller et al. |
| 6,338,790 | B1 | 1/2002 | Feldman et al. |
| 6,348,640 | B1 | 2/2002 | Navot et al. |
| 6,359,270 | B1 | 3/2002 | Bridson |
| 6,359,444 | B1 | 3/2002 | Grimes |
| 6,360,888 | B1 | 3/2002 | McIvor et al. |
| 6,361,503 | B1 | 3/2002 | Starobin et al. |
| 6,366,794 | B1 | 4/2002 | Moussy et al. |
| 6,377,828 | B1 | 4/2002 | Chaiken et al. |
| 6,377,852 | B1 | 4/2002 | Bornzin et al. |
| 6,377,894 | B1 | 4/2002 | Deweese et al. |
| 6,379,301 | B1 | 4/2002 | Worthington et al. |
| 6,381,493 | B1 | 4/2002 | Stadler et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,413,393 | B1 | 7/2002 | Van Antwerp et al. |
| 6,416,471 | B1 | 7/2002 | Kumar et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,440,068 | B1 | 8/2002 | Brown et al. |
| 6,461,496 | B1 | 10/2002 | Feldman et al. |
| 6,471,689 | B1 | 10/2002 | Joseph et al. |
| 6,478,736 | B1 | 11/2002 | Mault |
| 6,484,046 | B1 | 11/2002 | Say et al. |
| 6,493,069 | B1 | 12/2002 | Nagashimada et al. |
| 6,496,729 | B2 | 12/2002 | Thompson |
| 6,497,655 | B1 | 12/2002 | Linberg et al. |
| 6,498,043 | B1 | 12/2002 | Schulman et al. |
| 6,501,983 | B1 | 12/2002 | Natarajan et al. |
| 6,503,381 | B1 | 1/2003 | Gotoh et al. |
| 6,514,460 | B1 | 2/2003 | Fendrock |
| 6,514,718 | B2 | 2/2003 | Heller et al. |
| 6,520,326 | B2 | 2/2003 | McIvor et al. |
| 6,540,891 | B1 | 4/2003 | Stewart et al. |

(56) References Cited

U.S. PATENT DOCUMENTS 6,544,212 B2 4/2003 Galley et al.
6,546,268 B1 4/2003 Ishikawa et al.
6,549,796 B2 4/2003 Sohrab
6,551,494 B1 4/2003 Heller et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 * 5/2003 Heller .................... A61B 5/076 600/347
6,561,975 B1 5/2003 Pool et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,542 B1 6/2003 Houben et al.
6,572,545 B2 6/2003 Knobbe et al.
6,574,490 B2 6/2003 Abbink et al.
6,574,510 B2 6/2003 Von Arx et al.
6,576,101 B1 6/2003 Heller et al.
6,577,899 B2 6/2003 Lebel et al.
6,579,231 B1 6/2003 Phipps
6,579,690 B1 * 6/2003 Bonnecaze ............ A61B 5/746 435/14
6,585,644 B2 7/2003 Lebel et al.
6,591,125 B1 7/2003 Buse et al.
6,592,745 B1 7/2003 Feldman et al.
6,595,919 B2 7/2003 Berner et al.
6,600,997 B2 7/2003 Deweese et al.
6,605,200 B1 8/2003 Mao et al.
6,605,201 B1 8/2003 Mao et al.
6,607,509 B2 8/2003 Bobroff et al.
6,610,012 B2 8/2003 Mault
6,616,819 B1 9/2003 Liamos et al.
6,618,934 B1 9/2003 Feldman et al.
6,622,045 B2 9/2003 Snell et al.
6,633,772 B2 10/2003 Ford et al.
6,635,014 B2 10/2003 Starkweather et al.
6,635,167 B1 10/2003 Batman et al.
6,641,533 B2 11/2003 Causey, III et al.
6,648,821 B2 11/2003 Lebel et al.
6,650,471 B2 11/2003 Doi
6,654,625 B1 11/2003 Say et al.
6,656,114 B1 12/2003 Poulsen et al.
6,658,396 B1 12/2003 Tang et al.
6,659,948 B2 12/2003 Lebel et al.
6,668,196 B1 12/2003 Villegas et al.
6,675,030 B2 1/2004 Ciurczak et al.
6,676,816 B2 1/2004 Mao et al.
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,698,269 B2 3/2004 Baber et al.
6,702,857 B2 3/2004 Brauker et al.
6,730,200 B1 5/2004 Stewart et al.
6,731,976 B2 5/2004 Penn et al.
6,731,985 B2 5/2004 Poore et al.
6,733,446 B2 5/2004 Lebel et al.
6,735,183 B2 5/2004 O'Toole et al.
6,736,957 B1 5/2004 Forrow et al.
6,740,075 B2 5/2004 Lebel et al.
6,740,518 B1 5/2004 Duong et al.
6,741,877 B1 5/2004 Shults et al.
6,746,582 B2 6/2004 Heller et al.
6,749,740 B2 6/2004 Liamos et al.
6,758,810 B2 7/2004 Lebel et al.
6,764,581 B1 7/2004 Forrow et al.
6,770,030 B1 8/2004 Schaupp et al.
6,773,671 B1 8/2004 Lewis et al.
6,789,195 B1 9/2004 Prihoda et al.
6,790,178 B1 9/2004 Mault et al.
6,804,558 B2 10/2004 Haller et al.
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,850,790 B2 2/2005 Berner et al.
6,862,465 B2 3/2005 Shults et al.
6,865,407 B2 3/2005 Kimball et al.
6,873,268 B2 3/2005 Lebel et al.
6,878,112 B2 4/2005 Linberg et al.
6,881,551 B2 4/2005 Heller et al.
6,882,940 B2 4/2005 Potts et al.
6,892,085 B2 5/2005 McIvor et al.
6,893,545 B2 5/2005 Gotoh et al.
6,895,263 B2 5/2005 Shin et al.
6,895,265 B2 5/2005 Silver
6,923,763 B1 8/2005 Kovatchev et al.
6,923,764 B2 8/2005 Aceti et al.
6,931,327 B2 8/2005 Goode, Jr. et al.
6,932,892 B2 8/2005 Chen et al.
6,932,894 B2 8/2005 Mao et al.
6,936,006 B2 8/2005 Sabra
6,940,403 B2 9/2005 Kail, IV
6,941,163 B2 9/2005 Ford et al.
6,942,518 B2 9/2005 Liamos et al.
6,950,708 B2 9/2005 Bowman IV et al.
6,958,705 B2 10/2005 Lebel et al.
6,968,294 B2 11/2005 Gutta et al.
6,971,274 B2 12/2005 Olin
6,974,437 B2 12/2005 Lebel et al.
6,978,286 B2 12/2005 Francis et al.
6,983,176 B2 1/2006 Gardner et al.
6,990,366 B2 1/2006 Say et al.
6,997,907 B2 2/2006 Safabash et al.
6,998,247 B2 2/2006 Monfre et al.
7,003,336 B2 2/2006 Holker et al.
7,003,340 B2 2/2006 Say et al.
7,003,341 B2 2/2006 Say et al.
7,009,511 B2 3/2006 Mazar et al.
7,010,345 B2 3/2006 Hill et al.
7,015,817 B2 3/2006 Copley et al.
7,016,713 B2 3/2006 Gardner et al.
7,016,720 B2 3/2006 Kroll
7,020,508 B2 3/2006 Stivoric et al.
7,022,072 B2 4/2006 Fox et al.
7,022,219 B2 4/2006 Mansouri et al.
7,024,236 B2 4/2006 Ford et al.
7,024,245 B2 4/2006 Lebel et al.
7,025,425 B2 4/2006 Kovatchev et al.
7,027,848 B2 4/2006 Robinson et al.
7,027,931 B1 4/2006 Jones et al.
7,029,443 B2 4/2006 Kroll
7,029,444 B2 4/2006 Shin et al.
7,041,068 B2 5/2006 Freeman et al.
7,041,468 B2 5/2006 Drucker et al.
7,043,287 B1 5/2006 Khalil et al.
7,043,305 B2 5/2006 Kenknight et al.
7,046,153 B2 5/2006 Oja et al.
7,052,483 B2 5/2006 Wojcik
7,056,302 B2 6/2006 Douglas
7,058,453 B2 6/2006 Nelson et al.
7,060,031 B2 6/2006 Webb et al.
7,074,307 B2 7/2006 Simpson et al.
7,076,300 B1 7/2006 Kroll et al.
7,081,195 B2 7/2006 Simpson et al.
7,082,334 B2 7/2006 Boute et al.
7,092,891 B2 8/2006 Maus et al.
7,096,064 B2 8/2006 Deno et al.
7,098,803 B2 8/2006 Mann et al.
7,103,412 B1 9/2006 Kroll
7,108,778 B2 9/2006 Simpson et al.
7,110,803 B2 9/2006 Shults et al.
7,113,821 B1 9/2006 Sun et al.
7,118,667 B2 10/2006 Lee
7,123,950 B2 10/2006 Mannheimer
7,125,382 B2 10/2006 Zhou et al.
7,134,999 B2 11/2006 Brauker et al.
7,136,689 B2 11/2006 Shults et al.
7,142,911 B2 11/2006 Boileau et al.
7,153,265 B2 12/2006 Vachon

(56) References Cited

U.S. PATENT DOCUMENTS 7,155,290 B2 12/2006 Von Arx et al.
7,167,818 B2 1/2007 Brown
7,171,274 B2 1/2007 Starkweather et al.
7,174,199 B2 2/2007 Berner et al.
7,190,988 B2 3/2007 Say et al.
7,192,450 B2 3/2007 Brauker et al.
7,198,606 B2 4/2007 Boecker et al.
7,203,549 B2 4/2007 Schommer et al.
7,207,974 B2 4/2007 Safabash et al.
7,225,091 B2 5/2007 Tivig et al.
7,225,535 B2 6/2007 Feldman et al.
7,226,442 B2 6/2007 Sheppard, Jr. et al.
7,226,978 B2 6/2007 Tapsak et al.
7,228,182 B2 6/2007 Healy et al.
7,237,712 B2 7/2007 DeRocco et al.
7,258,673 B2 8/2007 Racchini et al.
7,267,665 B2 9/2007 Steil et al.
7,272,436 B2 9/2007 Gill et al.
7,276,029 B2 10/2007 Goode, Jr. et al.
7,278,983 B2 10/2007 Ireland et al.
7,286,894 B1 10/2007 Grant et al.
7,295,867 B2 11/2007 Berner et al.
7,297,114 B2 11/2007 Gill et al.
7,299,082 B2 11/2007 Feldman et al.
7,310,544 B2 12/2007 Brister et al.
7,317,938 B2 1/2008 Lorenz et al.
7,335,294 B2 2/2008 Heller et al.
7,347,819 B2 3/2008 Lebel et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,384,397 B2 6/2008 Zhang et al.
7,387,010 B2 6/2008 Sunshine
7,399,277 B2 7/2008 Saidara et al.
7,402,153 B2 7/2008 Steil et al.
7,404,796 B2 7/2008 Ginsberg
7,419,573 B2 9/2008 Gundel
7,424,318 B2 9/2008 Brister et al.
7,429,255 B2 9/2008 Thompson
7,460,898 B2 12/2008 Brister et al.
7,467,003 B2 12/2008 Brister et al.
7,471,972 B2 12/2008 Rhodes et al.
7,474,992 B2 1/2009 Ariyur
7,492,254 B2 2/2009 Bandy et al.
7,494,465 B2 2/2009 Brister et al.
7,497,827 B2 3/2009 Brister et al.
7,499,002 B2 3/2009 Blasko et al.
7,502,644 B2 3/2009 Gill et al.
7,519,408 B2 4/2009 Rasdal et al.
7,524,287 B2 4/2009 Bharmi
7,547,281 B2 6/2009 Hayes et al.
7,565,197 B2 7/2009 Haubrich et al.
7,569,030 B2 8/2009 Lebel et al.
7,574,266 B2 8/2009 Dudding et al.
7,583,990 B2 9/2009 Goode, Jr. et al.
7,591,801 B2 9/2009 Brauker et al.
7,599,726 B2 10/2009 Goode, Jr. et al.
7,602,310 B2 10/2009 Mann et al.
7,604,178 B2 10/2009 Stewart
7,613,491 B2 11/2009 Boock et al.
7,615,007 B2 11/2009 Shults et al.
7,618,369 B2 11/2009 Hayter et al.
7,630,748 B2 12/2009 Budiman
7,632,228 B2 12/2009 Brauker et al.
7,635,594 B2 12/2009 Holmes et al.
7,637,868 B2 12/2009 Saint et al.
7,640,048 B2 12/2009 Dobbles et al.
7,651,596 B2 1/2010 Petisce et al.
7,651,845 B2 1/2010 Doyle, III et al.
7,653,425 B2 1/2010 Hayter et al.
7,654,956 B2 2/2010 Brister et al.
7,659,823 B1 2/2010 Killian et al.
7,668,596 B2 2/2010 Von Arx et al.
7,699,775 B2 4/2010 Desai et al.
7,699,964 B2 4/2010 Feldman et al.
7,711,402 B2 5/2010 Shults et al.
7,713,574 B2 5/2010 Brister et al.
7,715,893 B2 5/2010 Kamath et al.
7,736,310 B2 6/2010 Taub
7,741,734 B2 6/2010 Joannopoulos et al.
7,766,829 B2 8/2010 Sloan et al.
7,768,386 B2 8/2010 Hayter et al.
7,768,387 B2 8/2010 Fennell
7,771,352 B2 8/2010 Shults et al.
7,774,145 B2 8/2010 Brauker et al.
7,775,444 B2 8/2010 DeRocco et al.
7,778,680 B2 8/2010 Goode, Jr. et al.
7,779,332 B2 8/2010 Karr et al.
7,782,192 B2 8/2010 Jeckelmann et al.
7,783,333 B2 8/2010 Brister et al.
7,791,467 B2 9/2010 Mazar et al.
7,792,562 B2 9/2010 Shults et al.
7,811,231 B2 10/2010 Jin et al.
7,813,809 B2 10/2010 Strother et al.
7,826,382 B2 11/2010 Sicurello et al.
7,826,981 B2 11/2010 Goode, Jr. et al.
7,831,310 B2 11/2010 Lebel et al.
7,860,574 B2 12/2010 Von Arx et al.
7,866,026 B1 1/2011 Wang et al.
7,882,611 B2 2/2011 Shah et al.
7,889,069 B2 2/2011 Fifolt et al.
7,899,511 B2 3/2011 Shults et al.
7,899,545 B2 3/2011 John
7,905,833 B2 3/2011 Brister et al.
7,912,674 B2 3/2011 Killoren Clark et al.
7,914,450 B2 3/2011 Goode, Jr. et al.
7,916,013 B2 3/2011 Stevenson
7,920,906 B2 4/2011 Goode, Jr. et al.
7,928,850 B2 4/2011 Hayter et al.
7,938,797 B2 5/2011 Estes
7,941,200 B2 5/2011 Weinert et al.
7,946,985 B2 5/2011 Mastrototaro et al.
7,955,258 B2 6/2011 Goscha et al.
7,970,448 B2 6/2011 Shults et al.
7,972,296 B2 7/2011 Braig et al.
7,974,672 B2 7/2011 Shults et al.
7,976,466 B2 7/2011 Ward et al.
7,978,063 B2 7/2011 Baldus et al.
7,999,674 B2 8/2011 Kamen
8,010,174 B2 8/2011 Goode, Jr. et al.
8,010,256 B2 8/2011 Oowada
8,160,900 B2 4/2012 Taub et al.
8,192,394 B2 6/2012 Estes et al.
8,216,138 B1 7/2012 McGarraugh
8,282,549 B2 10/2012 Brauker et al.
8,377,031 B2 2/2013 Hayter et al.
8,461,985 B2 6/2013 Fennell et al.
11,679,200 B2 6/2023 Hayter
2001/0037366 A1 11/2001 Webb et al.
2001/0048362 A1 12/2001 Spencer
2002/0019022 A1 2/2002 Dunn et al.
2002/0019612 A1 2/2002 Watanabe et al.
2002/0054320 A1 5/2002 Ogino
2002/0068860 A1 6/2002 Clark, Jr.
2002/0072784 A1 6/2002 Sheppard, Jr. et al.
2002/0095076 A1 7/2002 Krausman et al.
2002/0103499 A1 8/2002 Perez et al.
2002/0128594 A1 9/2002 Das et al.
2002/0130779 A1 9/2002 Ford
2002/0143266 A1 10/2002 Bock
2002/0147135 A1 10/2002 Schnell
2002/0169439 A1 11/2002 Flaherty
2002/0169635 A1 11/2002 Shillingburg
2002/0193679 A1 12/2002 Malave et al.
2003/0004403 A1 1/2003 Drinan et al.
2003/0021317 A1 1/2003 Liao et al.
2003/0023461 A1 1/2003 Quintanilla et al.
2003/0028089 A1 2/2003 Galley et al.
2003/0032867 A1 2/2003 Crothall et al.
2003/0050546 A1 3/2003 Desai et al.
2003/0055380 A1 3/2003 Flaherty
2003/0060692 A1 3/2003 L. Ruchti et al.
2003/0060753 A1 3/2003 Starkweather et al.

(56) References Cited

U.S. PATENT DOCUMENTS

2003/0100040 A1 5/2003 Bonnecaze et al.
2003/0100821 A1 5/2003 Heller et al.
2003/0114836 A1 6/2003 Estes et al.
2003/0114897 A1 6/2003 Von Arx et al.
2003/0130616 A1 7/2003 Steil et al.
2003/0147515 A1 8/2003 Kai et al.
2003/0167035 A1 9/2003 Flaherty et al.
2003/0168338 A1 9/2003 Gao et al.
2003/0191377 A1 10/2003 Robinson et al.
2003/0199790 A1 10/2003 Boecker et al.
2003/0208113 A1 11/2003 Mault et al.
2003/0212379 A1* 11/2003 Bylund .................. G16H 20/17 700/282
2003/0216630 A1 11/2003 Jersey-Willuhn et al.
2003/0217966 A1 11/2003 Tapsak et al.
2003/0225361 A1 12/2003 Sabra
2004/0010186 A1 1/2004 Kimball et al.
2004/0010207 A1 1/2004 Flaherty et al.
2004/0015131 A1 1/2004 Flaherty et al.
2004/0024553 A1 2/2004 Monfre et al.
2004/0034289 A1 2/2004 Teller et al.
2004/0039298 A1 2/2004 Abreu
2004/0041749 A1 3/2004 Dixon
2004/0054263 A1 3/2004 Moerman et al.
2004/0063435 A1 4/2004 Sakamoto et al.
2004/0064068 A1 4/2004 DeNuzzio et al.
2004/0064088 A1 4/2004 Gorman et al.
2004/0064096 A1 4/2004 Flaherty et al.
2004/0099529 A1 5/2004 Mao et al.
2004/0106858 A1 6/2004 Say et al.
2004/0122353 A1 6/2004 Shahmirian et al.
2004/0133164 A1 7/2004 Funderburk et al.
2004/0133390 A1 7/2004 Osorio et al.
2004/0135684 A1 7/2004 Steinthal et al.
2004/0138588 A1 7/2004 Saikley et al.
2004/0138716 A1 7/2004 Kon et al.
2004/0146909 A1 7/2004 Duong et al.
2004/0147872 A1 7/2004 Thompson
2004/0152622 A1 8/2004 Keith et al.
2004/0153032 A1 8/2004 Garribotto et al.
2004/0167464 A1 8/2004 Ireland et al.
2004/0167801 A1 8/2004 Say et al.
2004/0171921 A1 9/2004 Say et al.
2004/0172307 A1 9/2004 Gruber
2004/0176672 A1 9/2004 Silver et al.
2004/0186365 A1 9/2004 Jin et al.
2004/0197846 A1 10/2004 Hockersmith et al.
2004/0199056 A1 10/2004 Husemann et al.
2004/0204687 A1 10/2004 Mogensen et al.
2004/0204868 A1 10/2004 Maynard et al.
2004/0208780 A1 10/2004 Faries, Jr. et al.
2004/0219664 A1 11/2004 Heller et al.
2004/0236200 A1 11/2004 Say et al.
2004/0249420 A1 12/2004 Olson et al.
2004/0254433 A1 12/2004 Bandis et al.
2004/0254434 A1 12/2004 Goodnow et al.
2004/0260478 A1 12/2004 Schwamm
2004/0267300 A1 12/2004 Mace
2005/0001024 A1 1/2005 Kusaka et al.
2005/0003470 A1 1/2005 Nelson et al.
2005/0004439 A1 1/2005 Shin et al.
2005/0004494 A1 1/2005 Perez et al.
2005/0010087 A1 1/2005 Banet et al.
2005/0016276 A1 1/2005 Guan et al.
2005/0017864 A1 1/2005 Tsoukalis
2005/0027180 A1 2/2005 Goode, Jr. et al.
2005/0027181 A1 2/2005 Goode, Jr. et al.
2005/0027462 A1 2/2005 Goode, Jr. et al.
2005/0027463 A1 2/2005 Goode, Jr. et al.
2005/0031689 A1 2/2005 Shults et al.
2005/0038332 A1 2/2005 Saidara et al.
2005/0043598 A1 2/2005 Goode, Jr. et al.
2005/0049179 A1 3/2005 Davidson et al.
2005/0070774 A1 3/2005 Addison et al.
2005/0070777 A1 3/2005 Cho et al.
2005/0090607 A1 4/2005 Tapsak et al.
2005/0096516 A1 5/2005 Soykan et al.
2005/0113886 A1 5/2005 Fischell et al.
2005/0114068 A1 5/2005 Chey et al.
2005/0116683 A1 6/2005 Cheng et al.
2005/0121322 A1 6/2005 Say et al.
2005/0137530 A1 6/2005 Campbell et al.
2005/0143635 A1 6/2005 Kamath et al.
2005/0176136 A1 8/2005 Burd et al.
2005/0177398 A1 8/2005 Watanabe et al.
2005/0182306 A1 8/2005 Sloan
2005/0187442 A1 8/2005 Cho et al.
2005/0192494 A1 9/2005 Ginsberg
2005/0192557 A1* 9/2005 Brauker ............... A61B 5/4839 604/503
2005/0195930 A1 9/2005 Spital et al.
2005/0199494 A1 9/2005 Say et al.
2005/0204134 A1 9/2005 Von Arx et al.
2005/0214892 A1 9/2005 Kovatchev et al.
2005/0236361 A1 10/2005 Ufer et al.
2005/0241957 A1 11/2005 Mao et al.
2005/0245795 A1 11/2005 Goode, Jr. et al.
2005/0245799 A1 11/2005 Brauker et al.
2005/0245839 A1 11/2005 Stivoric et al.
2005/0245904 A1 11/2005 Estes et al.
2005/0251033 A1 11/2005 Scarantino et al.
2005/0272985 A1 12/2005 Kotulla et al.
2005/0277912 A1 12/2005 John
2005/0287620 A1 12/2005 Heller et al.
2005/0288725 A1 12/2005 Hettrick et al.
2006/0001538 A1 1/2006 Kraft et al.
2006/0001551 A1 1/2006 Kraft et al.
2006/0004270 A1 1/2006 Bedard et al.
2006/0010098 A1 1/2006 Goodnow et al.
2006/0015020 A1 1/2006 Neale et al.
2006/0017923 A1 1/2006 Ruchti et al.
2006/0020300 A1 1/2006 Nghiem et al.
2006/0025663 A1 2/2006 Talbot et al.
2006/0029177 A1 2/2006 Cranford, Jr. et al.
2006/0031094 A1 2/2006 Cohen et al.
2006/0058588 A1 3/2006 Zdeblick
2006/0079740 A1 4/2006 Silver et al.
2006/0091006 A1 5/2006 Wang et al.
2006/0142651 A1 6/2006 Brister et al.
2006/0154642 A1 7/2006 Scannell, Jr.
2006/0156796 A1 7/2006 Burke et al.
2006/0166629 A1 7/2006 Reggiardo
2006/0173260 A1 8/2006 Gaoni et al.
2006/0173406 A1 8/2006 Hayes et al.
2006/0189863 A1 8/2006 Peyser et al.
2006/0193375 A1 8/2006 Lee
2006/0202805 A1 9/2006 Schulman et al.
2006/0211072 A1 9/2006 Ryan et al.
2006/0224141 A1 10/2006 Rush et al.
2006/0226985 A1 10/2006 Goodnow et al.
2006/0229512 A1 10/2006 Petisce et al.
2006/0247508 A1 11/2006 Fennell
2006/0247685 A1 11/2006 Bharmi
2006/0247710 A1 11/2006 Goetz et al.
2006/0247985 A1 11/2006 Liamos et al.
2006/0253296 A1 11/2006 Liisberg et al.
2006/0258929 A1 11/2006 Goode, Jr. et al.
2006/0264785 A1 11/2006 Dring et al.
2006/0272652 A1 12/2006 Stocker et al.
2006/0276771 A1 12/2006 Galley et al.
2006/0281985 A1 12/2006 Ward et al.
2006/0287691 A1 12/2006 Drew
2006/0290496 A1 12/2006 Peeters
2006/0293607 A1 12/2006 Alt et al.
2007/0007133 A1 1/2007 Mang et al.
2007/0010950 A1 1/2007 Abensour et al.
2007/0016381 A1 1/2007 Kamath et al.
2007/0017983 A1 1/2007 Frank et al.
2007/0027381 A1 2/2007 Stafford
2007/0032706 A1 2/2007 Kamath et al.
2007/0032717 A1 2/2007 Brister et al.
2007/0033074 A1 2/2007 Nitzan et al.
2007/0038044 A1 2/2007 Dobbles et al.
2007/0055348 A1 3/2007 Pryor

(56) References Cited

U.S. PATENT DOCUMENTS

2007/0055799 A1 3/2007 Koehler et al.
2007/0056858 A1 3/2007 Chen et al.
2007/0060803 A1 3/2007 Liljeryd et al.
2007/0060814 A1 3/2007 Stafford
2007/0060869 A1 3/2007 Tolle et al.
2007/0060979 A1 3/2007 Strother et al.
2007/0066873 A1 3/2007 Kamath et al.
2007/0066956 A1 3/2007 Finkel
2007/0068807 A1 3/2007 Feldman et al.
2007/0071681 A1 3/2007 Gadkar et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0078818 A1 4/2007 Zivitz et al.
2007/0093786 A1 4/2007 Goldsmith et al.
2007/0094216 A1 4/2007 Mathias et al.
2007/0095661 A1 5/2007 Wang et al.
2007/0100222 A1 5/2007 Mastrototaro et al.
2007/0106135 A1 5/2007 Sloan et al.
2007/0108048 A1 5/2007 Wang et al.
2007/0118405 A1 5/2007 Campbell et al.
2007/0124002 A1 5/2007 Estes et al.
2007/0149874 A1 6/2007 Say et al.
2007/0149875 A1 6/2007 Ouyang et al.
2007/0153705 A1 7/2007 Rosar et al.
2007/0156094 A1 7/2007 Safabash et al.
2007/0168224 A1 7/2007 Letzt et al.
2007/0173706 A1 7/2007 Neinast et al.
2007/0173709 A1 7/2007 Petisce et al.
2007/0173710 A1 7/2007 Petisce et al.
2007/0173761 A1 7/2007 Kanderian, Jr. et al.
2007/0179349 A1 8/2007 Hoyme et al.
2007/0179352 A1 8/2007 Randlov et al.
2007/0179370 A1 8/2007 Say et al.
2007/0179434 A1 8/2007 Weinert et al.
2007/0191701 A1 8/2007 Feldman et al.
2007/0191702 A1 8/2007 Yodfat et al.
2007/0203407 A1 8/2007 Hoss et al.
2007/0203966 A1 8/2007 Brauker et al.
2007/0208244 A1 9/2007 Brauker et al.
2007/0208246 A1 9/2007 Brauker et al.
2007/0213657 A1* 9/2007 Jennewine ............. G16H 20/17
604/67
2007/0228071 A1 10/2007 Kamen et al.
2007/0232877 A1 10/2007 He
2007/0232878 A1 10/2007 Kovatchev et al.
2007/0232880 A1 10/2007 Siddiqui et al.
2007/0235331 A1 10/2007 Simpson et al.
2007/0244383 A1 10/2007 Talbot et al.
2007/0249922 A1 10/2007 Peyser et al.
2007/0253021 A1 11/2007 Mehta et al.
2007/0255321 A1 11/2007 Gerber et al.
2007/0255531 A1 11/2007 Drew
2007/0258395 A1 11/2007 Jollota et al.
2007/0270672 A1 11/2007 Hayter
2007/0271285 A1 11/2007 Eichorn et al.
2007/0282299 A1 12/2007 Hellwig
2007/0285238 A1 12/2007 Batra
2007/0287931 A1 12/2007 DiLorenzo
2007/0299617 A1 12/2007 Willis
2008/0009692 A1 1/2008 Stafford
2008/0018433 A1 1/2008 Pitt-Pladdy
2008/0021436 A1* 1/2008 Wolpert ................ A61B 5/1118
600/365
2008/0033254 A1 2/2008 Kamath et al.
2008/0039702 A1 2/2008 Hayter et al.
2008/0045824 A1 2/2008 Tapsak et al.
2008/0057484 A1 3/2008 Miyata et al.
2008/0058625 A1 3/2008 McGarraugh et al.
2008/0058626 A1 3/2008 Miyata et al.
2008/0058678 A1 3/2008 Miyata et al.
2008/0058773 A1 3/2008 John
2008/0060955 A1 3/2008 Goodnow
2008/0061961 A1 3/2008 John
2008/0064937 A1 3/2008 McGarraugh et al.
2008/0064943 A1 3/2008 Talbot et al.
2008/0071156 A1 3/2008 Brister et al.
2008/0071157 A1 3/2008 McGarraugh et al.
2008/0071158 A1 3/2008 McGarraugh et al.
2008/0071328 A1 3/2008 Haubrich et al.
2008/0083617 A1 4/2008 Simpson et al.
2008/0086042 A1 4/2008 Brister et al.
2008/0086044 A1 4/2008 Brister et al.
2008/0086273 A1 4/2008 Shults et al.
2008/0092638 A1 4/2008 Brenneman et al.
2008/0097289 A1 4/2008 Steil et al.
2008/0108942 A1 5/2008 Brister et al.
2008/0114228 A1 5/2008 McCluskey et al.
2008/0119703 A1 5/2008 Brister et al.
2008/0119705 A1 5/2008 Patel et al.
2008/0119710 A1 5/2008 Reggiardo et al.
2008/0139910 A1 6/2008 Mastrototaro et al.
2008/0154513 A1 6/2008 Kovatchev et al.
2008/0161666 A1 7/2008 Feldman et al.
2008/0167543 A1 7/2008 Say et al.
2008/0167572 A1 7/2008 Stivoric et al.
2008/0172205 A1 7/2008 Breton et al.
2008/0177149 A1 7/2008 Weinert et al.
2008/0182537 A1 7/2008 Manku et al.
2008/0183060 A1* 7/2008 Steil ............... C12Y 301/01003
606/151
2008/0183061 A1 7/2008 Goode et al.
2008/0183399 A1 7/2008 Goode et al.
2008/0188731 A1 8/2008 Brister et al.
2008/0188796 A1 8/2008 Steil et al.
2008/0189051 A1 8/2008 Goode et al.
2008/0194934 A1 8/2008 Ray et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195232 A1 8/2008 Carr-Brendel et al.
2008/0195967 A1 8/2008 Goode et al.
2008/0197024 A1 8/2008 Simpson et al.
2008/0199894 A1* 8/2008 Galasso ................. G16H 20/17
435/14
2008/0200788 A1 8/2008 Brister et al.
2008/0200789 A1 8/2008 Brister et al.
2008/0200791 A1 8/2008 Simpson et al.
2008/0201169 A1* 8/2008 Galasso ................. G16H 40/63
705/2
2008/0201325 A1 8/2008 Doniger et al.
2008/0208025 A1 8/2008 Shults et al.
2008/0208026 A1 8/2008 Noujaim et al.
2008/0208113 A1 8/2008 Damiano et al.
2008/0214900 A1 9/2008 Fennell et al.
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0228055 A1 9/2008 Sher
2008/0234663 A1 9/2008 Yodfat et al.
2008/0234943 A1 9/2008 Ray et al.
2008/0235053 A1 9/2008 Ray et al.
2008/0235469 A1 9/2008 Drew
2008/0242961 A1 10/2008 Brister et al.
2008/0242963 A1 10/2008 Essenpreis et al.
2008/0254544 A1 10/2008 Modzelewski et al.
2008/0255434 A1 10/2008 Hayter et al.
2008/0255437 A1 10/2008 Hayter
2008/0255438 A1 10/2008 Saidara et al.
2008/0255808 A1 10/2008 Hayter
2008/0256048 A1 10/2008 Hayter
2008/0262469 A1 10/2008 Brister et al.
2008/0267823 A1 10/2008 Wang et al.
2008/0269714 A1 10/2008 Mastrototaro et al.
2008/0269723 A1 10/2008 Mastrototaro et al.
2008/0275313 A1 11/2008 Brister et al.
2008/0287761 A1 11/2008 Hayter et al.
2008/0287762 A1 11/2008 Hayter et al.
2008/0287763 A1 11/2008 Hayter
2008/0288180 A1 11/2008 Hayter et al.

(56) References Cited

U.S. PATENT DOCUMENTS

| | | | |
|---|---|---|---|
| 2008/0288204 | A1 | 11/2008 | Hayter et al. |
| 2008/0296155 | A1 | 12/2008 | Shults et al. |
| 2008/0300572 | A1 | 12/2008 | Rankers et al. |
| 2008/0306368 | A1 | 12/2008 | Goode, Jr. et al. |
| 2008/0306434 | A1 | 12/2008 | Dobbles et al. |
| 2008/0306435 | A1 | 12/2008 | Kamath et al. |
| 2008/0306444 | A1 | 12/2008 | Brister et al. |
| 2008/0312518 | A1 | 12/2008 | Jina et al. |
| 2008/0312841 | A1 | 12/2008 | Hayter |
| 2008/0312842 | A1 | 12/2008 | Hayter et al. |
| 2008/0312844 | A1 | 12/2008 | Hayter et al. |
| 2008/0312845 | A1 | 12/2008 | Hayter et al. |
| 2008/0312859 | A1 | 12/2008 | Skyggebjerg et al. |
| 2008/0314395 | A1 | 12/2008 | Kovatchev et al. |
| 2008/0319085 | A1 | 12/2008 | Wright et al. |
| 2008/0319279 | A1 | 12/2008 | Ramsay et al. |
| 2008/0319295 | A1 | 12/2008 | Bernstein et al. |
| 2008/0319296 | A1 | 12/2008 | Bernstein et al. |
| 2009/0005665 | A1 | 1/2009 | Hayter et al. |
| 2009/0005666 | A1 | 1/2009 | Shin et al. |
| 2009/0006034 | A1 | 1/2009 | Hayter et al. |
| 2009/0006061 | A1 | 1/2009 | Thukral et al. |
| 2009/0006133 | A1 | 1/2009 | Weinert et al. |
| 2009/0012376 | A1 | 1/2009 | Agus |
| 2009/0012379 | A1 | 1/2009 | Goode, Jr. et al. |
| 2009/0018424 | A1 | 1/2009 | Kamath et al. |
| 2009/0018425 | A1 | 1/2009 | Ouyang et al. |
| 2009/0030294 | A1 | 1/2009 | Petisce et al. |
| 2009/0033482 | A1 | 2/2009 | Hayter et al. |
| 2009/0036747 | A1 | 2/2009 | Hayter et al. |
| 2009/0036760 | A1 | 2/2009 | Hayter |
| 2009/0036763 | A1 | 2/2009 | Brauker et al. |
| 2009/0040022 | A1 | 2/2009 | Finkenzeller |
| 2009/0043181 | A1 | 2/2009 | Brauker et al. |
| 2009/0043182 | A1 | 2/2009 | Brauker et al. |
| 2009/0043525 | A1 | 2/2009 | Brauker et al. |
| 2009/0043541 | A1 | 2/2009 | Brauker et al. |
| 2009/0043542 | A1 | 2/2009 | Brauker et al. |
| 2009/0045055 | A1 | 2/2009 | Rhodes et al. |
| 2009/0048503 | A1 | 2/2009 | Dalal et al. |
| 2009/0054745 | A1 | 2/2009 | Jennewine |
| 2009/0054747 | A1 | 2/2009 | Fennell |
| 2009/0054748 | A1 | 2/2009 | Feldman |
| 2009/0055149 | A1 | 2/2009 | Hayter et al. |
| 2009/0062633 | A1 | 3/2009 | Brauker et al. |
| 2009/0062635 | A1 | 3/2009 | Brauker et al. |
| 2009/0062767 | A1 | 3/2009 | Van Antwerp et al. |
| 2009/0063402 | A1 | 3/2009 | Hayter |
| 2009/0076356 | A1 | 3/2009 | Simpson et al. |
| 2009/0076360 | A1 | 3/2009 | Brister et al. |
| 2009/0076361 | A1 | 3/2009 | Kamath et al. |
| 2009/0082693 | A1 | 3/2009 | Stafford |
| 2009/0085768 | A1 | 4/2009 | Patel et al. |
| 2009/0085873 | A1 | 4/2009 | Betts et al. |
| 2009/0088614 | A1 | 4/2009 | Taub |
| 2009/0093687 | A1 | 4/2009 | Telfort et al. |
| 2009/0099436 | A1 | 4/2009 | Brister et al. |
| 2009/0105554 | A1 | 4/2009 | Stahmann et al. |
| 2009/0105560 | A1 | 4/2009 | Solomon |
| 2009/0105570 | A1 | 4/2009 | Sloan et al. |
| 2009/0105571 | A1 | 4/2009 | Fennell et al. |
| 2009/0105636 | A1 | 4/2009 | Hayter et al. |
| 2009/0112478 | A1 | 4/2009 | Mueller, Jr. et al. |
| 2009/0118589 | A1 | 5/2009 | Ueshima et al. |
| 2009/0124877 | A1 | 5/2009 | Goode, Jr. et al. |
| 2009/0124878 | A1 | 5/2009 | Goode, Jr. et al. |
| 2009/0124879 | A1 | 5/2009 | Brister et al. |
| 2009/0124964 | A1 | 5/2009 | Leach et al. |
| 2009/0131768 | A1 | 5/2009 | Simpson et al. |
| 2009/0131769 | A1 | 5/2009 | Leach et al. |
| 2009/0131776 | A1 | 5/2009 | Simpson et al. |
| 2009/0131777 | A1 | 5/2009 | Simpson et al. |
| 2009/0137886 | A1 | 5/2009 | Shariati et al. |
| 2009/0137887 | A1 | 5/2009 | Shariati et al. |
| 2009/0143659 | A1 | 6/2009 | Li et al. |
| 2009/0150186 | A1 | 6/2009 | Cohen et al. |
| 2009/0156919 | A1 | 6/2009 | Brister et al. |
| 2009/0163790 | A1 | 6/2009 | Brister et al. |
| 2009/0163791 | A1 | 6/2009 | Brister et al. |
| 2009/0164190 | A1 | 6/2009 | Hayter |
| 2009/0164239 | A1 | 6/2009 | Hayter et al. |
| 2009/0164251 | A1 | 6/2009 | Hayter |
| 2009/0178459 | A1 | 7/2009 | Li et al. |
| 2009/0182217 | A1 | 7/2009 | Li et al. |
| 2009/0189738 | A1 | 7/2009 | Hermle |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0198118 | A1 | 8/2009 | Hayter et al. |
| 2009/0204341 | A1 | 8/2009 | Brauker et al. |
| 2009/0216100 | A1 | 8/2009 | Ebner et al. |
| 2009/0216102 | A1 | 8/2009 | Say et al. |
| 2009/0216103 | A1 | 8/2009 | Brister et al. |
| 2009/0221890 | A1 | 9/2009 | Saffer et al. |
| 2009/0227855 | A1 | 9/2009 | Hill et al. |
| 2009/0234200 | A1 | 9/2009 | Husheer |
| 2009/0240120 | A1 | 9/2009 | Mensinger et al. |
| 2009/0240128 | A1 | 9/2009 | Mensinger et al. |
| 2009/0240193 | A1 | 9/2009 | Mensinger et al. |
| 2009/0240440 | A1 | 9/2009 | Shurabura et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0247857 | A1 | 10/2009 | Harper et al. |
| 2009/0247931 | A1 | 10/2009 | Damgaard-Sorensen |
| 2009/0253973 | A1 | 10/2009 | Bashan et al. |
| 2009/0267765 | A1 | 10/2009 | Greene et al. |
| 2009/0287073 | A1 | 11/2009 | Boock et al. |
| 2009/0287074 | A1 | 11/2009 | Shults et al. |
| 2009/0289796 | A1 | 11/2009 | Blumberg, Jr. |
| 2009/0292188 | A1 | 11/2009 | Hoss et al. |
| 2009/0296742 | A1 | 12/2009 | Sicurello et al. |
| 2009/0298182 | A1 | 12/2009 | Schulat et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299276 | A1 | 12/2009 | Brauker et al. |
| 2010/0010324 | A1 | 1/2010 | Brauker et al. |
| 2010/0010329 | A1 | 1/2010 | Taub et al. |
| 2010/0010331 | A1 | 1/2010 | Brauker et al. |
| 2010/0010332 | A1 | 1/2010 | Brauker et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0030038 | A1 | 2/2010 | Brauker et al. |
| 2010/0030053 | A1 | 2/2010 | Goode, Jr. et al. |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036225 | A1 | 2/2010 | Goode, Jr. et al. |
| 2010/0041971 | A1 | 2/2010 | Goode, Jr. et al. |
| 2010/0045465 | A1 | 2/2010 | Brauker et al. |
| 2010/0049024 | A1 | 2/2010 | Saint et al. |
| 2010/0056992 | A1 | 3/2010 | Hayter |
| 2010/0057040 | A1 | 3/2010 | Hayter |
| 2010/0057041 | A1 | 3/2010 | Hayter |
| 2010/0057042 | A1 | 3/2010 | Hayter |
| 2010/0057044 | A1 | 3/2010 | Hayter |
| 2010/0057057 | A1 | 3/2010 | Hayter et al. |
| 2010/0063372 | A1 | 3/2010 | Potts et al. |
| 2010/0063373 | A1 | 3/2010 | Kamath et al. |
| 2010/0076283 | A1 | 3/2010 | Simpson et al. |
| 2010/0081906 | A1 | 4/2010 | Hayter et al. |
| 2010/0081908 | A1 | 4/2010 | Dobbles et al. |
| 2010/0081909 | A1 | 4/2010 | Budiman et al. |

(56) References Cited

U.S. PATENT DOCUMENTS

| | | | |
|---|---|---|---|
| 2010/0081910 | A1 | 4/2010 | Brister et al. |
| 2010/0087724 | A1 | 4/2010 | Brauker et al. |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0105999 | A1 | 4/2010 | Dixon et al. |
| 2010/0119693 | A1 | 5/2010 | Tapsak et al. |
| 2010/0121169 | A1 | 5/2010 | Petisce et al. |
| 2010/0141656 | A1 | 6/2010 | Krieftewirth |
| 2010/0152554 | A1 | 6/2010 | Steine et al. |
| 2010/0160759 | A1 | 6/2010 | Celentano et al. |
| 2010/0168538 | A1 | 7/2010 | Keenan et al. |
| 2010/0168546 | A1 | 7/2010 | Kamath et al. |
| 2010/0174266 | A1 | 7/2010 | Estes |
| 2010/0185175 | A1 | 7/2010 | Kamen et al. |
| 2010/0190435 | A1 | 7/2010 | Cook et al. |
| 2010/0191082 | A1 | 7/2010 | Brister et al. |
| 2010/0213080 | A1 | 8/2010 | Celentano et al. |
| 2010/0234710 | A1 | 9/2010 | Budiman et al. |
| 2010/0240975 | A1 | 9/2010 | Goode, Jr. et al. |
| 2010/0274111 | A1 | 10/2010 | Say et al. |
| 2010/0280441 | A1 | 11/2010 | Wilinska et al. |
| 2010/0312176 | A1 | 12/2010 | Lauer et al. |
| 2010/0313105 | A1 | 12/2010 | Nekoomaram et al. |
| 2011/0004276 | A1 | 1/2011 | Blair et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |
| 2011/0028815 | A1 | 2/2011 | Simpson et al. |
| 2011/0028816 | A1 | 2/2011 | Simpson et al. |
| 2011/0031986 | A1 | 2/2011 | Bhat et al. |
| 2011/0077490 | A1 | 3/2011 | Simpson et al. |
| 2011/0148905 | A1 | 6/2011 | Simmons et al. |
| 2011/0152637 | A1 | 6/2011 | Kateraas et al. |
| 2011/0208027 | A1 | 8/2011 | Wagner et al. |
| 2011/0208155 | A1 | 8/2011 | Palerm et al. |
| 2011/0257895 | A1 | 10/2011 | Brauker et al. |
| 2011/0287528 | A1 | 11/2011 | Fern et al. |
| 2011/0320130 | A1 | 12/2011 | Valdes et al. |
| 2012/0078071 | A1 | 3/2012 | Bohm et al. |
| 2012/0108934 | A1 | 5/2012 | Valdes et al. |
| 2012/0165626 | A1 | 6/2012 | Irina et al. |
| 2012/0165640 | A1 | 6/2012 | Galley et al. |
| 2012/0173200 | A1 | 7/2012 | Breton et al. |
| 2012/0190989 | A1 | 7/2012 | Kaiser et al. |
| 2012/0215462 | A1 | 8/2012 | Goode, Jr. et al. |
| 2013/0035575 | A1 | 2/2013 | Mayou et al. |
| 2013/0235166 | A1 | 9/2013 | Jones et al. |
| 2014/0114154 | A1* | 4/2014 | Kamath ............... A61B 5/1495 600/345 |

FOREIGN PATENT DOCUMENTS

| | | | |
|---|---|---|---|
| EP | 0390390 | A1 | 10/1990 |
| EP | 0396788 | A1 | 11/1990 |
| EP | 0127958 | B1 | 3/1992 |
| EP | 0286118 | B1 | 1/1995 |
| EP | 1677668 | B1 | 7/2010 |
| WO | WO 1999056613 | A1 | 11/1999 |
| WO | WO 2000059370 | A1 | 10/2000 |
| WO | WO 2001052935 | A1 | 7/2001 |
| WO | WO 2001054753 | A2 | 8/2001 |
| WO | WO 2003082091 | A2 | 10/2003 |
| WO | WO 2004009161 | A1 | 1/2004 |
| WO | WO 2006079867 | A1 | 8/2006 |
| WO | WO 2007097754 | A1 | 8/2007 |
| WO | WO 2008030347 | A2 | 3/2008 |
| WO | WO 2008143943 | A1 | 11/2008 |
| WO | WO 2008/151452 | A1 | 12/2008 |
| WO | WO 2009/049252 | A1 | 4/2009 |
| WO | WO 2009146119 | A2 | 12/2009 |

OTHER PUBLICATIONS

Summary of Safety and Effectiveness Data for STS-7 Continuous Glucose Monitoring System, Notice of Approval dated May 31, 2007; 14 pages; Anlage TW 11 D5b, Taylor Wessing, Statement of Defence in *Abbott* v. *Dexcom*, Opposition to EP 3782539.

Letter from Department of Health and Human Services to DexCom Inc. regarding STS-7 Continuous Glucose Monitoring System, dated May 31, 2007; 95 pages; Anlage TW 25, Taylor Wessing, Statement of Defence in *Abbott* v. *Dexcom*, Opposition to EP 3782539.

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1070.

Bennion, N., et al., "Alternate Site Glucose Testing: A Crossover Design", Diabetes Technology & Therapeutics, vol. 4, No. 1, 2002, pp. 25-33.

Blank, T. B., et al., "Clinical Results From a Non-Invasive Blood Glucose Monitor", Optical Diagnostics and Sensing of Biological Fluids and Glucose and Cholesterol Monitoring II, Proceedin2:s of SPIE vol. 4624, 2002, pp. 1-10.

Blendea, M. C., et al., "Heart Disease in Diabetic Patients", Current Diabetes Reports, vol. 3, 2003, pp. 223-229.

Bremer, T. M., et al., "Benchmark Data from the Literature for Evaluation of New Glucose Sensing Technologies", Diabetes Technology & Therapeutics, vol. 3, No. 3, 2001, pp. 409-418.

Brooks, S. L., et al., "Development of an On-Line Glucose Sensor for Fermentation Monitoring", Biosensors, vol. 3, 1987/88, pp. 45-56.

Cass, A. E., et al., "Ferrocene-Medicated Enzyme Electrode for Amperometric Determination of Glucose", Analytical Chemistry vol. 56 No. 4, 1984, 667-671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607-613.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

"Dexcom's 7-Day Continuous Glucose Monitoring System," Jun. 1, 2007, https://newatlas.com/; 1 page.

Diabetes Control and Complications Trial Research Group, "The Effect of Intensive Treatment of Diabetes on the Development and Progression of Long-Term Complications in Insulin-Dependent Diabetes Mellitus", New England J. Med., vol. 329, No. 13, 1993, pp. 977-986.

Eckert, B. et al. "Hypoglycaemia leads to an increased QT interval in normal men", Clinical Physiology, vol. 18, No. 6, 1998, pp. 570-575.

El-Khatib, F. H., et al., "Adaptive Closed-Loop Control Provides Blood-Glucose Regulation Using Subcutaneous Insulin and Glucagon Infusion in Diabetic Swine", Journal of Diabetes Science and Technolo!!V vol. 1 No. 2, 2007, pp. 181-192.

Exhibit CP-6, Second Expert Report of Dr. Cesar C. Palerm, Oct. 21, 2022, Bailey, T.S. et al., "Reduction in Hemoglobin Ale with Real-Time Continuous Glucose Monitoring: Results from a 12-Week Observational Study" Diabetes Technology & Therapeutics, 2007, 9(3):203-210.

Exhibit CP-7, Second Expert Report of Dr. Cesar C. Palerm, Oct. 21, 2022, Garg, S. et al., "Improvement in Glycemic Excursions with a Transcutaneous, Real-Time Continuous Glucose Sensor", Diabetes Care, 2006, 29(12):44-50.

Exhibit CP-8, Second Expert Report of Dr. Cesar C. Palerm, Oct. 21, 2022, Garg, S. et al, Relationship of Fasting and Hourly Blood Glucose Levels to HbAlc Values, Diabetes Care, 2006, 6(12):2644-2649.

Exhibit No. 11, to the Expert Report of Professor Nick Oliver, Sep. 20, 2022, "The Effect of Intensive Treatment of Diabetes on the Development and Progression of Long-Term Complications in

(56) References Cited

OTHER PUBLICATIONS

Insulin-Dependent Diabetes Mellitus" The New England Journal of Medicine, 1993, 329(14):977-986.

Exhibit No. 12, to the Expert Report of Professor Nick Oliver, Sep. 20, 2022, National Service Framework for Diabetes: Standards, Dept. of Health, 2002, 48 pages.

Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.

Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.

Exhibit No. 2, to the Expert Report of Professor Nick Oliver, Sep. 20, 2022, "Note for Guidance on Clinical Investigation of Medicinal Products in the Treatment of Diabetes Mellitus," The European Agency for the Evaluation of Medicinal Products, 2002, 12 pages.

Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.

Exhibit No. 21, to the Expert Report of Professor Nick Oliver, Sep. 20, 2022, Devries, J.H. "Glucose Sensing Issues for the Artificial Pancreas" Journal of Diabetes Science and Technology, 2008, 2(4):732-734.

Exhibit No. 23, to the Expert Report of Professor Nick Oliver, Sep. 20, 2022, Internet Archive, WayBack Machine, Medtronic MiniMed, 2004, 20 pages.

Exhibit No. 24, to the Expert Report of Professor Nick Oliver, Sep. 20, 2022, "Glucowatch G2, Automatic Glucose Biographer and Autosensors," 2002, 70 pages.

Exhibit No. 25, to the Expert Report of Professor Nick Oliver, Sep. 20, 2022, "Guardian® REAL-Time Continuous Glucose Monitoring System, User Guide," Medtronic MiniMed, 2006, 181 pages.

Exhibit No. 26, to the Expert Report of Professor Nick Oliver, Sep. 20, 2022, "CGMS® iProTM Continuous Glucose Recorder, User Guide," Medtronic MiniMed, 2007, 36 pages.

Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.

Exhibit No. 30, to the Expert Report of Professor Nick Oliver, Sep. 20, 2022, Revised specification for publication No. US2007208244AI, 2007, 170 pages.

Exhibit No. 31, to the Expert Report of Professor Nick Oliver, Sep. 20, 2022, Revised Specification for EP625, 2008, 30 pages.

Exhibit No. 32, to the Expert Report of Professor Nick Oliver, Sep. 20, 2022, Puhr, S. et al., "Real-World Hypoglycemia Avoidance with a Predictive Low Glucose Alert Does Not Depend on Frequent Screen Views", Journal of Diabetes Sciences and Technology, 2004, 14(1): 83-86.

Exhibit No. 4, to the Expert Report of Professor Nick Oliver, Sep. 20, 2022, Amiel, S. A., et al., "Hypoglycaemia in Type 2 diabetes", Diabetic Medicine, 2008, 25:245-254.

Feldman, B., et al., "A Continuous Glucose Sensor Based on Wired EnzymeIM Technology—Results from a 3-Day Trial in Patients with Type 1 Diabetes", Diabetes Technology & TheraDeutics vol. 5 No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor PamDhlet, 2004.

Freestyle Navigator Continuous Glucose Monitoring System, User's Guide, Abbott Diabetes Care Inc., May 2008; 195 pages.

Garg, S., et al., "Improvement in Glycemic Excursions with a Transcutaneous, Real-Time Continuous Glucose Sensor", Diabetes Care, vol. 29, No. 1, 2006, pp. 44-50.

Georgescu, B., et al., "Real-Time Multi-model Tracking of Myocardium in Echocardiography Using Robust Information Fusion", Medical Image Computing and Computer-Assisted Intervention, 2004, pp. 777-785.

Goldman, J.M., et al., "Masimo Signal Extraction Pulse Oximetry", Journal of Clinical Monitoring and Computing, vol. 16, No. 7, 2000, pp. 475-483.

Harris, N.D., et al., "Can Changes in QT Interval be used to Predict the Onset of Hypoglycemia in Type 1 Diabetes?," Computers in Cardiology, vol. 27, 2000, pp. 375-378.

Heller, S. R., "Abnormalities of the electrocardiogram during hypoglycemia: the cause of the dead in bed syndrome?," International Journal of Clinical Practice, Suppl. No. 129, 2002, pp. 27-32.

Isermann, R., "Supervision, Fault-Detection and Fault-Diagnosis Methods—An Introduction", Control En2:ineerin2: Practice vol. 5 No. 5, 1997, pp. 639-652.

Isermann, R., et al., "Trends in the Application of Model-Based Fault Detection and Diagnosis of Technical Processes", Control En2:ineerin2: Practice vol. 5 No. 5, 1997, pp. 709-719.

Johnson, P. C., "Peripheral Circulation", John Wiley & Sons, 1978, pp. 198.

Jones, T. W., et al., "Mild Hypoglycemia and Impairment of Brain Stem and Cortical Evoked Potentials in Healthy Subjects," Diabetes, vol. 39, 1990, pp. 1550-1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", IEEE Press, 2004, pp. 141, 142, 548, 549.

Kuure-Kinsey, M., et al., "Dual-Rate Kalman Filter for Continuous Glucose Monitoring", Proceedings of the 28th IEEE, EMBS Annual International Conference, New York City, 2006, pp. 63-66.

Landstedt-Hallin, L., et al., "Increased QT dispersion during hypoglycaemia in patients with type 2 diabetes mellitus," Journal ofInternal Medicine, vol. 246, 1999, pp. 299-307.

Li, Y., et al., "In Vivo Release From a Drug Delivery MEMS Device", Journal of Controlled Release, vol. 100, 2004, pp. 211-219.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, vol. 5. No. 4, 2003, pp. 573-587.

Lortz, J., et al., "What is Bluetooth? We Explain The Newest Short-Range Connectivity Technology", Smart ComQuting Learning Series, Wireless ComQuting, vol. 8, Issue 5, 2002, pp. 72-74.

Maher, R. C., "A Method for Extrapolation of Missing Digital Audio Data", Preprints of Papers Presented at the AES Convention, 1993, pp. 1-19.

Maher, R.C., "Audio Enhancement using Nonlinear Time-Frequency Filtering", AES 26th International Conference, 2005, pp. 1-9.

Malin, S. F., et al., "Noninvasive Prediction of Glucose by Near-Infrared Diffuse Reflectance Spectoscopy", Clinical Chemisty, vol. 45, No. 9, 1999, pp. 1651-1658.

Malmberg, K., "Prospective randomised study of intensive insulin treatment on long-term survival after acute myocardial infarction in patients with diabetes mellitus", British Medical Journal, vol. 314, 1997, pp. 1512-1515.

Markel, A., et al., "Hypoglycaemia-Induced Ischaemic ECG Changes", La Presse Medicale, vol. 23, No. 2, 1994, pp. 78-79.

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", Diabetes Technology & TheraDeutics vol. 3 No. 3, 2001, pp. 367-376.

(56) References Cited

OTHER PUBLICATIONS

Mckean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.
Morbiducci, U., et al., "Improved Usability of the Minimal Model ofInsulin Sensitivity Based on an Automated Approach and Genetic Algorithms for Parameter Estimation", Clinical Science, vol. 112, 2007, pp. 257-263.
Mougiakakou, et al., "A Real Time Simulation Model of Glucose-Insulin Metabolism for Type 1 Diabetes Patients", Proceedings of the 2005 IEEE 2005, pp. 298-301.
Okin, P. M., et al., "Electrocardiogramapolarization Complexity and Abnormality Predict All-Cause and Cardiovascular Mortality in Diabetes," Diabetes, vol. 53, 2004, pp. 434-440.
Panteleon, A. E., et al., "The Role of the Independent Variable to Glucose Sensor Calibration", Diabetes Technology & Therapeutics, vol. 5, No. 3, 2003, pp. 401-410.
Parker, R., et al., "Robust Hoo Glucose Control in Diabetes Using a Physiological Model", AIChE Journal, vol. 46, No. 12, 2000, pp. 2537-2549.
PCT/US2009/055453 ISR and Written Opinion, dated Oct. 20, 2009.
PCT/US2009/055454 ISR and Written Opinion, dated Oct. 20, 2009.
PCT/US2009/055455 ISR and Written Opinion, dated Oct. 7, 2009.
PCT/US2009/055457 ISR and Written Opinion, dated Nov. 13, 2009.
PCT/US2009/055458 ISR and Written Opinion, dated Oct. 7, 2009.
PCT/US2009/055459 ISR and Written Opinion, dated Oct. 22, 2009.
Peterson, K.G., et al., "Regulation of Serum Potassium During Insulin-Induced Hypoglycemia", Diabetes, vol. 31, 1982, pp. 615-617.
Pickup, J., et al., "Implantable Glucose Sensors: Choosing the Appropriate Sensing Strategy", Biosensors, vol. 3, 1987/88, pp. 335-346.
Pickup, J., et al., "In Vivo Molecular Sensing in Diabetes Mellitus: An Implantable Glucose Sensor with Direct Electron Transfer", Diabetologia vol. 32, 1989, pp. 213-217.
Pishko, M. V., et al., "Amperometric Glucose Microelectrodes Prepared Through Immobilization of Glucose Oxidase in Redox Hydrogels", Analytical Chemistzy, vol. 63, No. 20, 1991, pp. 2268-2272.
PMA Approvals FDA—webpage available at: https://www.fda.gov; 3 pages.
PMA database search for Freestyle Navigator Continuous Glucose Monitor—https://www.fda.gov; 6 pages.
Quinn, C. P., et al., "Kinetics of Glucose Delivery to Subcutaneous Tissue in Rats Measured with 0.3-nun Amperometric Microsensors", The American Physiological Society, 1995, EI55-EI61.
Rana, B. S., et al., "Relation of QT Interval Dispersion to the Number of Different Cardiac Abnormalities in Diabetes Mellitus", The American Journal of Cardiology, vol. 90, 2002, pp. 483-487.
Robinson, R. T. C. E., et al. "Changes in cardiac repolarization during clinical episodes of nocturnal hypoglycaemia in adults with Type 1 diabetes," Diabetologia, vol. 47, 2004, pp. 312-315.
Rodriguez, N., et al., "Flexible Communication and Control Protocol for Injectable Neuromuscular Interfaces", IEEE Transactions on Biomedical Circuits and Systems, vol. 1, No. 1, 2007, pp. 19-27.
Roe, J. N., et al., "Bloodless Glucose Measurements", Critical Review in Therapeutic Drug Carrier Systems vol. 15 Issue 3, 1998, pp. 199-241.
Sakakida, M., et al., "Development ofFerrocene-Mediated Needle-Type Glucose Sensor as a Measure of True Subcutaneous Tissue Glucose Concentrations", Artificial Organs Today, vol. 2, No. 2, 1992, pp. 145-158.
Sakakida, M., et al., "Ferrocene-Mediated Needle-Type Glucose Sensor Covered with Newly Desie.ned Biocompatible Membrane", Sensors and Actuators B, vol. 13-14, 1993, nn. 319-322.
Salehi, C., et al., "A Telemetry-Instrumentation System for Long-Term Implantable Glucose and Oxygen Sensors", Analytical Letters vol. 29 No. 13, 1996, pp. 2289-2308.
Sandham, William et al., "Blood Glucose Prediction for Diabetes Therapy Using a Recurrent Artificial Neural Network," 9th European Signal Processing Conference (EUSIPCO 1998), 1998, pp. 1-4.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Glycaemic Control in Pancreatectomized Dogs with a Wearable Artificial Endocrine Pancreas", Diabetologia. vol. 24, 1983, pp. 179-184.
Shichiri, M., et al., "In Vivo Characteristics of Needle-Type Glucose Sensor—Measurements of Subcutaneous Glucose Concentrations in Human Volunteers", Hormone and Metabolic Research Sunnlement Series vol. 20, 1988, nn. 17-20.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loon Prosthetic Systems Chanter 15, 1985, nn. 197-210.
Shichiri, M., et al., "Telemetry Glucose Monitoring Device With Needle-Type Glucose Sensor: AU seful Tool for Blood Glucose Monitoring in Diabetic Individuals", Diabetes Care, vol. 9, No. 3, 1986, pp. 298-301.
Shichiri, M., et al., "Wearable Artificial Endocrine Pancreas With Needle-Type Glucose Sensor", The Lancet, 1982, nn. 1129-1131.
Shults, M. C., et al., "A Telemetry-Instrumentation System for Monitoring Multiple Subcutaneously Implanted Glucose Sensors", IEEE Transactions on Biomedical Engineering, vol. 41 No. 10 1994, pp. 937-942.
Sparacino, Giovanni et al., "Glucose Concentration can be Predicted Ahead in Time From Continuous Glucose Monitoring Sensor Time-Series," IEEE Transactions on Biomedical Engineering, Vo. 54, No. 5, May 2007; 7 pages.
Steinhaus, B. M., et al., "The Information Content of the Cardiac Electrogram at the Stimulus Site," Annual International Conference of the IEEE Engineering in Medicine and Biology Society, vol. 12, No. 2, 1990, pp. 0607-0609.
Sternberg, R., et al., "Study and Development of Multilayer Needle-Type Enzyme-Based Glucose Microsensors", Biosensors, vol. 4, 1988, pp. 27-40.
Thompson, M., et al., "In Vivo Probes: Problems and Perspectives", Clinical Biochemistry, vol. 19, 1986, pp. 255-261.
Turner, A., et al., "Diabetes Mellitus: Biosensors for Research and Management", Biosensors, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring_ Chanter 4, 1997, pp. 117-137.
Velho, G., et al., "Strategies for Calibrating a Subcutaneous Glucose Sensor", Biomedica Biochimica Acta, vol. 48, 1989, pp. 957-964.
Whipple, G., "Low Residual Noise Speech Enhancement Utilizing Time-Frequency", Proceedings of the International Conference on Acoustics, Speech, and Signal Processing, vol. 19, 1994, pp. 15-18.
Wilson, G. S., et al., "Progress Toward the Development of an Implantable Sensor for Glucose", Clinical Chemistry, vol. 38, No. 9, 1992, pp. 1613-1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.

* cited by examiner

100

CLOSED LOOP CONTROL AND SIGNAL ATTENUATION DETECTION

CROSS-REFERENCE TO RELATED APPLICATIONS

The present application is a continuation of U.S. patent application Ser. No. 16/252,973, filed Jan. 21, 2019, which is a continuation of U.S. patent application Ser. No. 15/184,961, filed Jun. 16, 2016, which is a continuation of U.S. patent application Ser. No. 12/202,304, filed Aug. 31, 2008, all of which are incorporated herein by reference in their entireties for all purposes.

BACKGROUND

Benefits of a closed loop control system for treating diabetic conditions with monitoring glucose levels and adjusting delivery rate of insulin are well known. Such systems, referred to as artificial pancreas, model healthy pancreas which, when functioning normally, produces insulin (by the beta cells (β-cells)) to counteract the rise in glucose levels in the blood stream. As is known, Type-1 diabetes mellitus condition exists when the beta cells in the pancreas either die or are unable to produce sufficient amount of insulin naturally in response to the elevated glucose levels.

Common treatment of Type-1 diabetes is the use of insulin pumps that are programmed to continuously deliver insulin to the body through an infusion set. The use of insulin pumps to treat Type-2 diabetes (where the beta cells in the pancreas do produce insulin, but an inadequate quantity) is also becoming more prevalent. Such insulin delivery devices are preprogrammed with delivery rates such as basal profiles which are tailored to each user, and configured to provide the needed insulin to the user. Additionally, the preprogrammed delivery rates may be supplemented with periodic administration of bolus dosages of insulin (for example, correction bolus or carbohydrate bolus) as may be needed by the user.

In addition, continuous glucose monitoring systems have been developed to allow real time monitoring of fluctuation in glucose level. One example is the FreeStyle Navigator® Continuous Glucose Monitoring System available from Abbott Diabetes Care Inc., of Alameda, Calif. The use of such glucose monitoring systems provides the user with real time glucose level information. Using the continuous glucose monitoring system, for example, diabetics are able to determine when insulin is needed to lower glucose levels or when additional glucose is needed to raise the level of glucose.

With the continued rise in the number of diagnosed diabetic conditions, there is on-going research to develop closed loop control systems to automate the insulin delivery based on the real time monitoring of the fluctuation in the glucose levels. Closed loop control algorithms such as, for example, proportional, plus integral, plus derivative (PID) control algorithm or model predictive control algorithm exist and are used to control the automatic delivery of insulin based on the glucose levels monitored. One key concern in such automated systems is safety. For example, the glucose sensor in the closed loop control system may enter failure mode (permanently or temporarily) in which case the monitored glucose level in the closed loop control system will introduce error and potentially result in undesirable or dangerous amount of insulin being administered. Additionally, the infusion component in the closed loop control system may have errors or experience failure modes that results in an inaccurate amount of insulin delivered to the user.

Indeed, safety considerations as well as accuracy considerations to address and/or minimize the potential unreliability in the components of the closed loop control system are important to provide a robust control system in the treatment of diabetic conditions.

SUMMARY

In one aspect, there are provided a method and device for monitoring a plurality of parameters associated with a closed loop control operation including continuously monitoring a physiological condition and automatic administration of a medication, detecting a signal level associated with the monitored physiological condition deviating from a predetermined threshold level, retrieving the medication level administered associated with a time period of the detected signal level, applying the retrieved medication level to the detected signal based on a predefined predictive model to generate a predictive signal, and comparing the detected signal to the predictive signal to determine whether a condition associated with the detected signal level is present.

In another aspect, there are provided a method and device for monitoring control parameters in a closed loop control operation including continuously monitoring a physiological condition and automatic administration of a medication, determining glucose response level based on a predictive model including a delivery rate of the administered medication, comparing the determined glucose response level to a time corresponding analyte sensor signal based on the monitored physiological condition to determine a sensor signal condition, and executing a corrective procedure when the determined sensor signal condition based on the comparison indicates an adverse signal condition.

Also provided are systems and kits.

DETAILED DESCRIPTION

Figure 1:
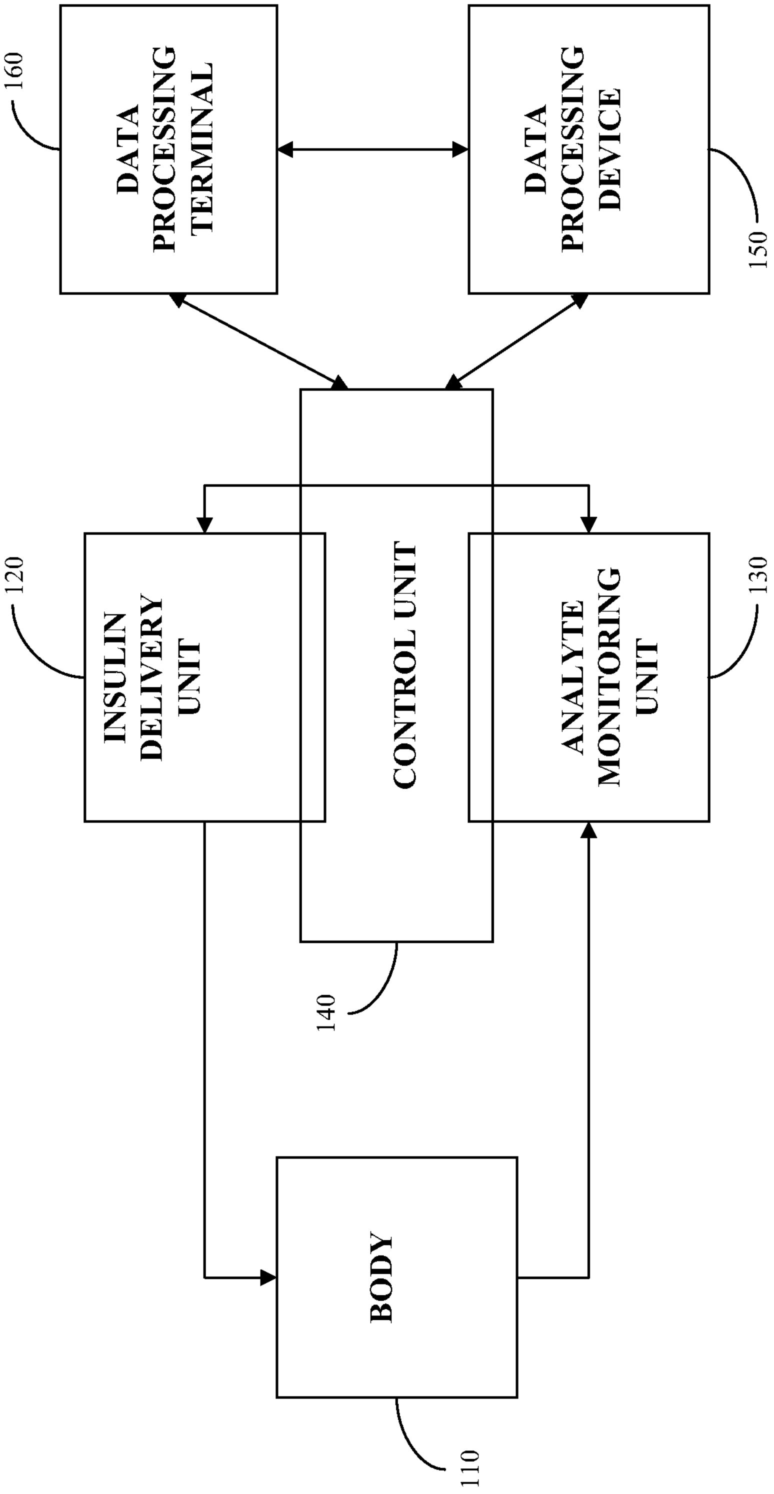
FIG. 1 is a block diagram illustrating an overall closed loop control system in accordance with one embodiment of the present disclosure.

Before embodiments of the present disclosure are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms “a”, “an”, and “the” include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and system for a robust closed loop control system with safety parameters for continuously monitoring at least one analyte such as glucose in body fluid and delivering suitable level of medication such as insulin. In certain embodiments, the present disclosure relates to the continuous and/or automatic in vivo monitoring of the level of an analyte using an analyte sensor, and under the control of a closed loop control algorithm, determining and delivering an appropriate level of medication such as insulin in response to the monitored analyte level.

Embodiments includes medication delivery devices such as external infusion pumps, implantable infusion pumps, on-body patch pump, or any other processor controlled medication delivery devices that are in communication with one or more control units which also control the operation of the analyte monitoring devices. The medication delivery devices may include one or more reservoirs or containers to hold the medication for delivery in fluid connection with an infusion set, for example, including an infusion tubing and/or cannula. The cannula may be positioned so that the medication is delivered to the user or patient at a desired location, such as, for example, in the subcutaneous tissue under the skin layer of the user.

Embodiments include analyte monitoring devices and systems that include an analyte sensor—least a portion of which is positionable beneath the skin of the user—for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc.

A sensor (and/or a sensor insertion apparatus) may be, for example, configured to be positionable in a patient for the continuous or periodic monitoring of a level of an analyte in a patient’s dermal fluid. For the purposes of this description, continuous monitoring and periodic monitoring will be used interchangeably, unless noted otherwise.

The analyte level may be correlated and/or converted to analyte levels in blood or other fluids. In certain embodiments, an analyte sensor may be configured to be positioned in contact with dermal fluid to detect the level of glucose, which detected glucose may be used to infer the glucose level in the patients bloodstream. For example, analyte sensors may be insertable through the skin layer and into the dermal layer under the skin surface at a depth of approximately 3 mm under the skin surface and containing dermal fluid. Embodiments of the analyte sensors of the subject disclosure may be configured for monitoring the level of the analyte over a time period which may range from minutes, hours, days, weeks, months, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time, the rate of change of the analyte, etc. Predictive alarms may notify the control unit (and/or the user) of predicted analyte levels that may be of concern in advance of the analyte level reaching the future level. This enables the control unit to determine a priori a suitable corrective action and implement such corrective action.

FIG. 1 is a block diagram illustrating an overall closed loop control system in accordance with one embodiment of the present disclosure. Referring to FIG. 1, in one aspect, the closed loop control system 100 includes an insulin delivery unit 120 that is connected to a body 110 of a user or patient to establish a fluid path to deliver medication such as insulin. In one aspect, the insulin delivery unit 120 may include an infusion tubing fluidly connecting the reservoir of the delivery unit 120 to the body 110 using a cannula with a portion thereof positioned in the subcutaneous tissue of the body 110.

Referring to FIG. 1, the system 100 also includes an analyte monitoring device 130 that is configured to monitor the analyte level in the body 110. As shown in FIG. 1, a control unit 140 is provided to control the operation of the insulin delivery unit 120 and the analyte monitoring unit 130. In one embodiment, the control unit 140 may be a processor based control unit having provided therein one or more closed loop control algorithm to control the operation of the analyte monitoring device 130 and the delivery unit 120. In one aspect, the control unit 140, the analyte monitoring unit 130 and the delivery unit 120 may be integrated in a single housing. In other embodiments, the control unit 140 may be provided in the housing of the delivery unit 120 and configured for communication (wireless or wired) with the analyte monitoring unit 130. In an alternate embodiment, the control unit may be integrated in the housing of the analyte monitoring unit 130 and configured for communication (wireless or wired) with the delivery unit 120. In yet another embodiment, the control unit 140 may be a separate component of the overall system 100 and configured for communication (wireless or wired) with both the delivery unit 120 and the analyte monitoring unit 130.

Referring back to FIG. 1, the analyte monitoring unit 130 may include an analyte sensor that is transcutaneously positioned through a skin layer of the body 110, and in signal communication with a compact data transmitter provided on the skin layer of the body 110 which is configured to transmit the monitored analyte level substantially in real time to the analyte monitoring unit 130 for processing and/or display. In another aspect, the analyte sensor may be wholly implantable in the body 110 with a data transmitter and configured to wirelessly transmit the monitored analyte level to the analyte monitoring unit 130.

Referring still to FIG. 1, also shown in the overall system 100 is a data processing device 150 in signal communication with the one or more of the control unit 140, delivery unit 120 and the analyte monitoring unit 130. In one aspect, the data processing device 150 may include an optional or supplemental device in the closed loop control system to provide user input/output functions, data storage and processing. Examples of the data processing device 150 include, but not limited to mobile telephones, personal digital assistants (PDAs), in vitro blood glucose meters, Blackberry® devices, iPhones, Palm® devices, data paging devices, and the like each of which include an output unit such as one or more of a display, audible and/or vibratory output, and/or an input unit such as a keypad, keyboard, input buttons and the like, and which are configured for communication (wired or wireless) to receive and/or transmit data, and further, which include memory devices such as random access memory, read only memory, volatile and/or non-volatile memory that store data.

Also shown in the overall system 100 is a data processing terminal 160 which may include a personal computer, a server terminal, a laptop computer, a handheld computing device, or other similar computing devices that are configured to data communication (over the internet, local area network (LAN), cellular network and the like) with the one or more of the control unit 140, the delivery unit 120, the analyte monitoring unit 130, or the data processing device 150, to process, analyze, store, archive, and update information.

It is to be understood that the analyte monitoring device 130 of FIG. 1 may be configured to monitor a variety of analytes at the same time or at different times. Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

Additional detailed descriptions of embodiments of the continuous analyte monitoring device and system, calibrations protocols, embodiments of its various components are provided in U.S. Pat. Nos. 6,175,752; 6,284,478; 7,299,082; U.S. patent application Ser. No. 10/745,878 filed Dec. 26, 2003 entitled "Continuous Glucose Monitoring System and Methods of Use", each incorporated by reference in its entirety for all purposes. Additional detailed description of systems including medication delivery units and analyte monitoring devices, embodiments of the various components are provided in U.S. patent application Ser. No. 11/386,915, entitled "Method and System for Providing Integrated Medication Infusion and Analyte Monitoring System", the disclosure of which is incorporated by reference for all purposes. Moreover, additional detailed description of medication delivery devices and its components are provided in U.S. Pat. No. 6,916,159, the disclosure of which is incorporated by reference for all purposes.

Referring back to FIG. 1, each of the components shown in the system 100 may be configured to be uniquely identified by one or more of the other components in the system so that communication conflict may be readily resolved between the various components, for example, by exchanging or pre-storing and/or verifying unique device identifiers as part of communication between the devices, by using periodic keep alive signals, or configuration of one or more devices or units in the overall system as a master-slave arrangement with periodic bidirectional communication to confirm integrity of signal communication therebetween.

Further, data communication may be encrypted or encoded (and subsequently decoded by the device or unit receiving the data), or transmitted using public-private keys, to ensure integrity of data exchange. Also, error detection and/or correction using, for example, cyclic redundancy check (CRC) or techniques may be used to detect and/or correct for errors in signals received and/or transmitted between the devices or units in the system 100. In certain aspects, data communication may be responsive to a command or data request received from another device in the system 100, while some aspects of the overall system 100 may be configured to periodically transmit data without prompting (such as the data transmitter, for example, in the analyte monitoring unit 130 periodically transmitting analyte related signals.

In certain embodiments, the communication between the devices or units in the system 100 may include one or more of an RF communication protocol, an infrared communication protocol, a Bluetooth enabled communication protocol, an 802.11x wireless communication protocol, internet connection over a data network or an equivalent wireless communication protocol which would allow secure, wireless communication of several units (for example, per HIPPA requirements) while avoiding potential data collision and interference.

In certain embodiments, data processing device 150, analyte monitoring unit 130 and/or delivery unit 120 may include blood glucose meter functions or capability to receive blood glucose measurements. For example, the housing of these devices may include a strip port to receive a blood glucose test strip with blood sample to determine the blood glucose level. Alternatively, a user input device such as an input button or keypad may be provided to manually enter such information. Still further, upon completion of a blood glucose measurement, the result may be wirelessly and/or automatically transmitted to another device in the system 100. For example, it is desirable to maintain a certain level of water tight seal on the housing of the delivery unit 120 during continuous use by the patient or user. In such case, incorporating a strip port to receive a blood glucose test strip may be undesirable. As such, the blood glucose meter function including the strip port may be integrated in the housing of another one of the devices or units in the system (such as in the analyte monitoring unit 103 and/or data processing device 150). In this case, the result from the blood glucose test, upon completion may be wirelessly transmitted to the delivery unit 120 for storage and further processing.

Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® or Precision® blood glucose test strips from Abbott Diabetes Care Inc. Glucose information obtained by the in vitro glucose testing device may be used for a variety of purposes, computations, etc. For example, the information may be used to calibrate the analyte sensor, confirm results of the sensor to increase the confidence in the accuracy level thereof (e.g., in instances in which information obtained by sensor is employed in therapy related decisions), determine suitable amount of bolus dosage for administration by the delivery unit 120

In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is obtained firstly. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate.

One or more devices or components of the system 100 may include an alarm system that, e.g., based on information from control unit 140, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels reach or exceed a threshold value. An alarm system may also, or alternatively, be activated when the rate of change or acceleration of the rate of change in analyte level increase or decrease reaches or exceeds a threshold rate of change or acceleration. For example, in the case of the glucose monitoring unit 130, an alarm system may be activated if the rate of change in glucose concentration exceeds a threshold value which might indicate that a hyperglycemic or hypoglycemic condition is likely to occur. In the case of the delivery unit 120, alarms may be associated with occlusion conditions, low reservoir conditions, malfunction or anomaly in the fluid delivery and the like. System alarms may also notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Referring yet again to FIG. 1, the control unit 140 of the closed loop control system 100 may include one or more processors such as microprocessors and/or application specific integrated circuits (ASIC), volatile and/or non-volatile memory devices, and additional components that are configured to store and execute one or more closed loop control algorithms to dynamically control the operation of the delivery unit 120 and the analyte monitoring unit 130. The one or more closed loop control algorithms may be stored as a set of instructions in the one or more memory devices and executed by the one or more processors to vary the insulin delivery level based on, for example, glucose level information received from the analyte sensor.

As discussed in further detail below, the one or more control algorithms of the control unit 140 are configured to monitor parameters and conditions associated with a safety indication of the closed loop control system 100 and generate and notify the user, as may be desirable to perform one or more troubleshooting actions and/or automatically revert to a semi-closed loop control mode or a manual control mode that require some level of user, patient or healthcare provider intervention.

Figure 2:
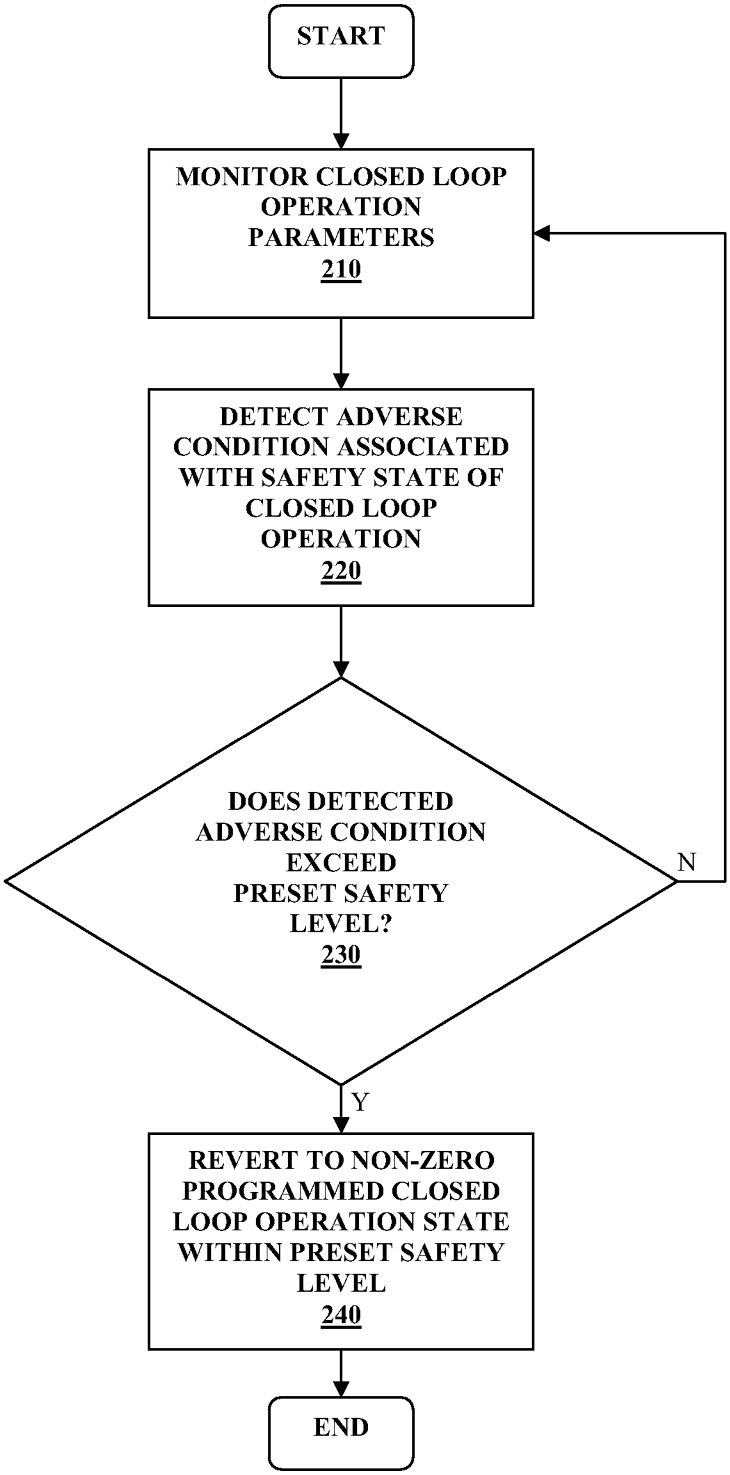
FIG. 2 is a flowchart illustrating adverse condition monitoring and control in a closed loop control system in accordance with one embodiment of the present disclosure.

FIG. 2 is a flowchart illustrating adverse condition monitoring and control in a closed loop control system in accordance with one embodiment of the present disclosure.

Referring to FIGS. 1 and 2, in one embodiment, control unit 140 executing the closed loop system control is configured to monitor the closed loop control operation parameters (210). In one aspect, the closed loop control operation parameters may be associated with the operation of the delivery unit 120, and operational conditions associated therewith such as fluid delivery, amount of insulin delivered, potential occlusion and the like. In addition the closed loop control operation parameters monitored may also include operational conditions associated with the analyte monitoring unit 130 such as, for example, the validity or integrity of analyte sensor signals, unanticipated sensor signal drop out, missing sensor data, and the like. Further, in embodiments where the delivery unit 120 and analyte monitoring unit 130 are separate components in the system 100 communicating via wireless connection, monitored control operation parameters may include the integrity of the communication connection between the devices or units in the system 100.

Referring to FIG. 2, when based on the monitored closed loop operation parameters an adverse condition associated with a safety state of the closed loop operation is detected (220), it is determined whether the detected adverse condition exceeds a preset safety level (230). For example, in the case where the adverse condition is associated with the integrity of analyte sensor signals, it is determined whether sufficiently accurate glucose level can be derived based on the received sensor signals (for example, based on extrapolation using previously received sensor data, and/or in conjunction with a rate of change of glucose level determination). The adverse condition detected may also include a determined medication delivery level that exceeds a preset threshold level (for example, a physician determined maximum basal delivery rate for the user). As a further example, the adverse condition detected may include communication failure between the components of the overall system 100 including, the analyte monitoring unit 130 and the delivery unit 120.

Referring back to FIG. 2, when it is determined that the detected adverse condition does not exceed a preset safety level, in one aspect, the control unit 140 is configured to proceed with the execution of the closed loop control algorithm based on the real time glucose data received from the analyte monitoring unit 130 to adjust the insulin delivery rate from the delivery unit 120, and the routine returns to monitoring the closed loop operation parameters. On the other hand, if it is determined that the detected adverse condition exceeds the preset safety level, the control unit 140 in one embodiment is configured to command or instruct the delivery unit 120 to revert to a non-zero pre-programmed closed loop operation state within the safety level (240). For example, when it is determined that the determined insulin level for delivery exceeds the safety level or maximum delivery rate (for example, established by a physician or healthcare provider, or the user, and programmed and stored in the control unit 140), the control unit 140 is configured to automatically revert to an insulin delivery rate that is within the safety level so that potential over-dosing may be avoided.

In another aspect, the control unit 140 may be configured to issue a command to the delivery unit 120 every 15 minutes (or some other predetermined time interval) which sets insulin delivery rate for a 20 minute time period (or some other suitable time period). In the event that the adverse condition exceeding the preset safety level is detected preventing the control unit 140 to issue a new command to the delivery unit 120 during the 20 minute time period, the control unit 140 is configured to instruct the delivery unit 120 to revert to a pre-programmed delivery rate that is within the safety level (for example, a less amount of insulin to be delivered). In a further aspect, the detected adverse condition may include a determination of insulin on board value that, in conjunction with the insulin amount to be delivered exceeds the upper safely level of insulin delivery, the control unit 140 may be configured to revert to or switch to a preset or pre-programmed level that would bring the insulin delivery amount to be within the determined safety level.

As discussed, in one aspect, the insulin delivery amount that is within the safety level may be pre-programmed in the control unit 140, for example, and implemented as part of the closed loop control to automatically deliver the insulin amount based on the pre-programmed level. In a further aspect, the control unit 140 may be configured to modify or adjust the existing insulin delivery rate that is within the safety level in response to the detected adverse condition, (for example, reducing the determined insulin delivery rate by a certain factor such as 75%, to maintain the insulin delivery amount within the safety level).

In this manner, in one aspect, when adverse condition associated with the safety state of the closed loop control operation, the control unit 140 may be configured to operate within a predefined safety range rather than requesting user intervention or disabling the closed loop control operation to revert to a manual control operation mode. While certain examples of adverse conditions are discussed above, within the scope of the present disclosure, any other condition associated with the safety level in the operation of the closed loop control system 100 are contemplated, the detection of any of which initiates the evaluation of the detected condition and appropriate modification to the closed loop control system parameters to continue operation of the closed loop control operation without prematurely disabling the system, while maintaining the desired level of safety in using the closed loop control system 100.

Figure 3:
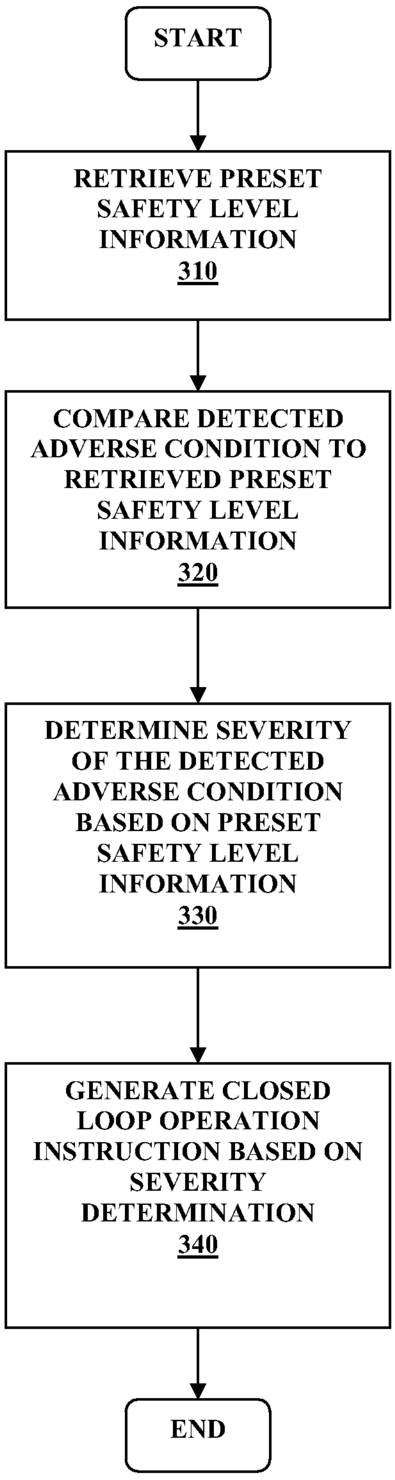
FIG. 3 is a flowchart illustrating adverse condition monitoring and control in a closed loop control system in accordance with another embodiment of the present disclosure.

FIG. 3 is a flowchart illustrating adverse condition monitoring and control in a closed loop control system in accordance with another embodiment of the present disclosure. Referring to FIGS. 1 and 3, in one embodiment, control unit 140 (FIG. 1) retrieves a preset safety level information (310) and compares the retrieved preset safety level information to one or more detected adverse condition (320). Thereafter, a level of severity associated with the detected adverse condition is determined based, at least in part on the retrieved preset safety level information (330). After determining the severity level, the control unit 140 is configured to generate one or more closed loop operation instructions based on the determined severity level for execution.

That is, in one aspect, when an adverse condition is detected by the control unit 140, the control unit 140 (FIG. 1) is configured in one aspect to determine how severe is the detected adverse condition with respect to the automated insulin delivery. For example, control unit 140 may detect a communication failure from the transmitter of the analyte monitoring unit 130 and thus not receive a current sensor data indicative of the glucose level. However, the control unit 140 may have stored in one or more of its memory units previously received glucose levels from the transmitter of the analyte monitoring unit 130. Given an insulin delivery rate that is within the safety level, and a relatively stable glucose value (for example, based on a rate of change of glucose determination from previously received glucose data), the control unit 140 may be configured to declare the communication failure as a non-critical adverse condition detected. In this manner, the generated closed loop operation instruction (340) may not modify the current delivery rate by the delivery unit 120 (FIG. 1).

On the other hand, if the rate of change of the glucose level indicated by previously received sensor data demonstrates a rapid variation in the glucose level, and/or the communication failure persists over a time period that exceeds a certain level (for example, exceeding 20 minutes or some other suitable time frame), the generated closed loop operation instruction (340) may include commands to the delivery unit 120 (FIG. 1) to modify the delivery rate and/or revert to a pre-programmed delivery rate that are within the previously determined safety level. In one aspect, the control unit 140 (FIG. 1) may be configured to continuously monitor the presence of the detected adverse condition until the condition is corrected, in which case, the generated closed loop operation instruction (340) may include commands to the delivery unit 120 to return to the prior closed loop control operation.

Figure 4:
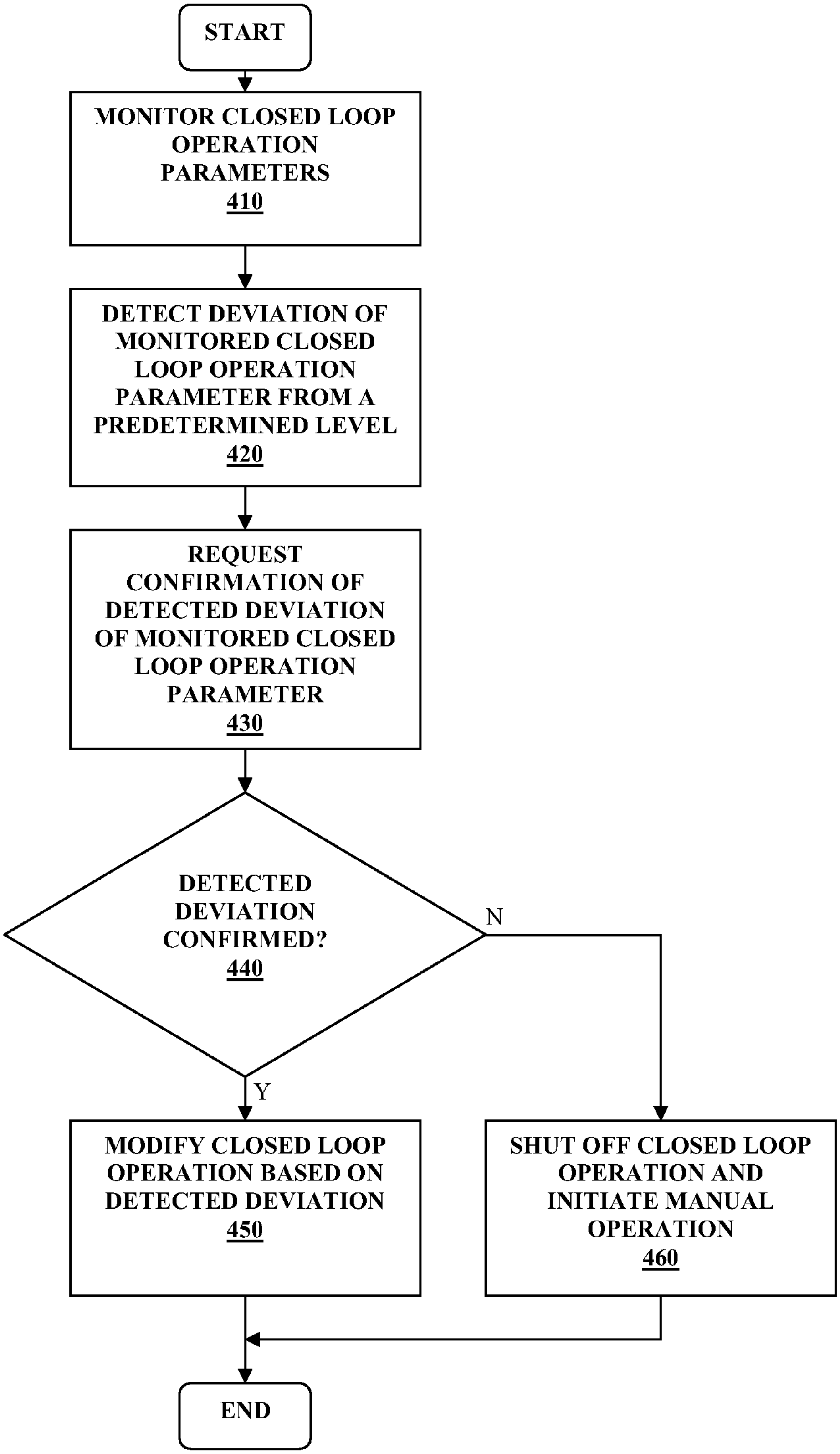
FIG. 4 is a flowchart illustrating condition deviation monitoring and control in a closed loop control system in accordance with one embodiment of the present disclosure.

FIG. 4 is a flowchart illustrating condition deviation monitoring and control in a closed loop control system in accordance with one embodiment of the present disclosure. Referring to FIGS. 1 and 4, in another aspect, control unit 140 (FIG. 1) monitors the closed loop operation parameters (410) and when it detects one or more monitored closed loop operation parameters deviating from a predetermined level (420), the control unit 140 (FIG. 1) may be configured to generate and output a request for confirmation of the detected deviation of the monitored closed loop operation parameter (430).

For example, in the closed loop control system 100 (FIG. 1), a user interface such as a display unit or audible/vibratory notification in the insulin delivery unit 120 and/or the analyte monitoring unit 130 may indicate a notification for the user to confirm the presence of the detected deviation of the monitored closed loop operation parameter. Referring to FIG. 4, if the detected deviation of the monitored closed loop operation parameter is confirmed (440), in one aspect, the control unit 140 (FIG. 1) may be configured to modify the closed loop control operation based on the detected deviation of one or more of its parameters (450). On the other hand, if the presence of the detected deviation of the monitored closed loop operation parameter is not confirmed, then the control unit 140 (FIG. 1) may be configured to disable the closed loop control operation, and initiate a manual operation mode (460) to deliver insulin by the delivery unit 120 (FIG. 1).

In this manner, in one aspect, the control unit 140 (FIG. 1) may be configured to request for user confirmation or verification of the presence of the detected adverse condition prior to initiating responsive corrective action, and further, when no verification or confirmation is received, for example, within a set time period, the control unit 140 (FIG. 1) may be configured to disable the closed loop control operation. Accordingly, certain adverse conditions detected may prompt the control unit 140 (FIG. 1) to request confirmation prior to automatically responding to such occurrence of adverse condition, and further, when no confirmation is received, the control unit 140 (FIG. 1) may temporarily revert to a semi-closed loop or non-closed loop manual delivery mode. In this manner, in certain aspects, a level of safety in using the closed loop control system 100 is maintained, and depending upon the particular detected adverse condition, the control unit 140 may automatically, temporarily adjust the delivery mode of the delivery unit 120 (FIG. 1), or alternatively, require user intervention.

Furthermore, within the scope of the present disclosure, while the detected conditions are described as adverse conditions, any parameter or condition associated with the operation of the closed loop control system 100 are contemplated including but not limited to, analyte sensor operation, sensor signal filtering, sensor signal level, sensor calibration, sensor signal attenuation, communication failure, signal outlier condition, rate of change of the glucose level, insulin delivery rate, insulin on board information, type of insulin, duration of the closed loop control operation, number or frequency of bolus dosage administration, predicted or projected glucose level and/or the direction of the predicted or projected glucose level, frequency of blood glucose measurements, maximum or minimum insulin delivery level, for example.

Figure 5:
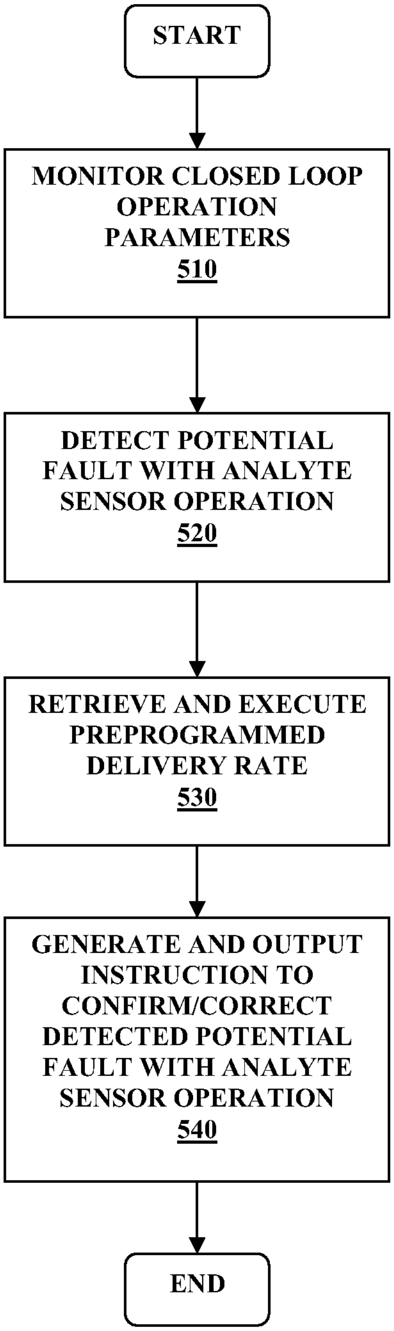
FIG. 5 is a flowchart illustrating analyte sensor condition monitoring and control in a closed loop control system in accordance with one embodiment of the present disclosure.

FIG. 5 is a flowchart illustrating analyte sensor condition monitoring and control in a closed loop control system in accordance with one embodiment of the present disclosure. Referring to FIGS. 1 and 5, in one embodiment, control unit 140 (FIG. 1) is configured to monitor closed loop operation parameters (510) in the closed loop control system 100 (FIG. 1). When a potential fault or failure mode associated with the operation of the analyte sensor is detected (520), the control unit 140 is configured to retrieve and execute a preprogrammed delivery rate (530) (for example, a predetermined basal profile), while maintaining the closed loop control operation mode. Further, the control unit 140 is configured to generate and output instructions or request to confirm and/or correct the detected potential fault or failure mode of the analyte sensor (540).

That is, in one aspect, the closed loop control operation is not disabled when it is initially detected that the analyte sensor may not be properly functioning. Rather, the closed loop control operation includes the execution of a pre-programmed delivery rate that is determined to be within a safety level, and when the potential fault condition or failure mode has been corrected, the control unit 140 may be configured to terminate the execution of the pre-programmed delivery rate and resume real time automatic adjustment to the insulin delivery rate based on the analyte sensor signals.

In this manner, rather than prematurely terminating the operation of the closed loop control system 100 at a first indication of potential failure or fault of the analyte sensor, in one aspect, the control unit 140 is configured to instruct the delivery unit 120 to execute a predetermined delivery rate that is within the safety level until corrective action related to the analyte sensor (for example, replacing the sensor, or recalibrating the sensor with a blood glucose measurement) is performed. In a further aspect, the control unit 140 may be configured to modify the retrieved predetermined delivery rate based on the insulin delivered (for example, to consider the insulin on board level) so that the safety level associated with the amount of insulin to be delivered is maintained.

Figure 6:
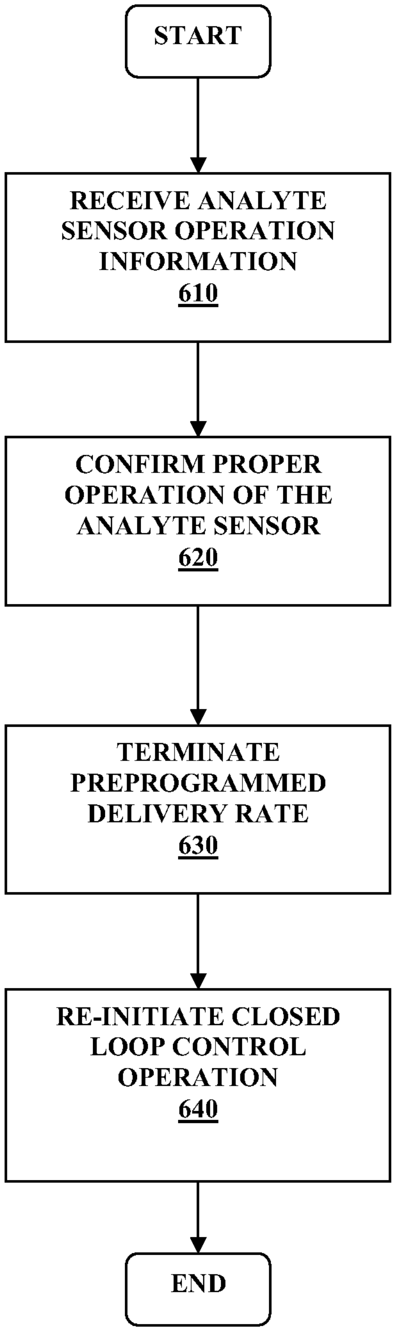
FIG. 6 is a flowchart illustrating analyte sensor condition monitoring and control in a closed loop control system in accordance with another embodiment of the present disclosure.

FIG. 6 is a flowchart illustrating analyte sensor condition monitoring and control in a closed loop control system in accordance with another embodiment of the present disclosure. Referring to FIGS. 1 and 6, in another aspect, when the control unit 140 receives analyte sensor operation information (610), one or more routines are performed to confirm the proper operation of the analyte sensor (620). For example, the control unit 140 may be configured to verify the calibration information of the analyte sensor so that the value level derived therefrom accurately indicates the monitored glucose level.

In a further aspect, the control unit 140 may be configured to retrieve the most recent sensor sensitivity determination based, for example, on the reference blood glucose measurement received, and to compare the retrieved sensitivity to a stored nominal sensitivity for the sensor to confirm a variation between sensitivities not exceeding a predetermined level. In another aspect, when a scheduled calibration event occurs to calibrate the analyte sensor, the current blood glucose measurement is used to determine an updated sensor sensitivity value which may be used in conjunction with one or more prior sensitivity values or nominal sensitivity value.

Referring back to FIG. 6, when it is confirmed that the analyte sensor is in proper operation mode, the preprogrammed delivery rate executed by the delivery unit 120 (FIG. 1) initiated when the sensor potential failure mode was detected, is terminated (630), and the closed loop control operation based on the analyte sensor signals is re-initiated (640).

In the manner described above, in accordance with embodiments of the present disclosure, the operation of the closed loop control system 100 may include monitoring the condition or parameters associated with the analyte monitoring unit 130 and for example, the analyte sensor, and execute one or more routines to instruct the delivery unit 120 to temporarily execute preprogrammed or modified delivery profile determined to be within the safety limits, or to disable the closed loop control operation to maintain the desired degree of safety in using the closed loop control system 100

(FIG. 1). Indeed, in one aspect, for example, when an analyte sensor reading erroneously indicates a high level of glucose which is a false positive value and where the actual glucose level is lower than the measured high level of glucose, aspects of the closed loop control operation are configured to establish a limit in the amount of insulin delivered so that when sensor failure is detected, delivery of insulin amount beyond the determined safe level is prevented.

Figure 7:
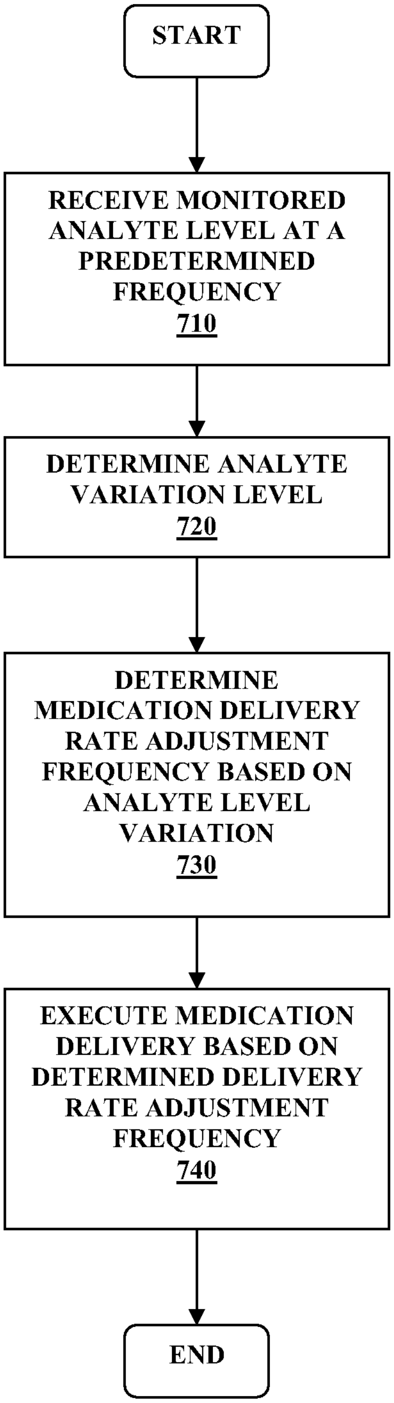
FIG. 7 is a flowchart illustrating variable rate control in a closed loop control system in accordance with one embodiment of the present disclosure.

FIG. 7 is a flowchart illustrating variable rate control in a closed loop control system in accordance with one embodiment of the present disclosure. Referring to FIGS. 1 and 7, in one aspect, control unit 140 executing the closed loop control algorithm in the closed loop control system 100 receives monitored analyte level at a predetermined frequency (710). Based at least in part of the received monitored analyte level, the analyte variation level is determined (720) Thereafter, as shown, the medication delivery rate adjustment frequency is determined based on the determined analyte variation level (730), and thereafter, the delivery unit 120 (FIG. 1) is instructed to deliver the medication at the determined medication delivery rate adjustment frequency (740). That is, in one aspect, the rate of monitored glucose level is associated with the adjustment of the frequency in which to instruct the delivery unit 120 to deliver insulin.

For example, in one aspect, the control unit 140 may be configured to monitor the glucose level from the analyte monitoring unit 130 at a higher frequency (such as, for example once per minute), and also, adjust the rate of insulin delivery by the delivery unit 120 (FIG. 1) at a lower frequency (for example, once every 15 minutes). Indeed, it may be unnecessary to adjust the rate of insulin delivery more frequently than once every 15 minutes when the monitored glucose level (at a higher frequency) does not indicate significant variation in the glucose level. Accordingly, control unit 140 may be configured to issue an instruction or command to the delivery unit 120 once every 15 minutes (or some other suitable interval) to vary the delivery rate based on the glucose level.

One advantage resulting from the less frequent delivery rate adjustment is the conservation of power in the control unit 140 and/or the delivery unit 120. That is, battery power may be conserved by avoiding the generation, communication and/or execution of instructions or commands associated with determining and implementing modification to the insulin delivery rate. On the other hand, since the glucose level is monitored every minute (or at a more frequent time interval), control unit 140 is configured to monitor the variation in the glucose level monitored, and as long as the variation is within a threshold level, the corresponding insulin level delivery adjustment determination is not executed with the same or similar frequency.

However, when the variation in the monitored glucose level exceeds the predetermined threshold level indicating a large variation in the monitored glucose level, or in the cases where a meal event or carbohydrate intake event occurs which will impact the monitored glucose level, it may be desirable to adjust the rate of insulin delivery to be more frequent (for example, adjustment to the delivery rate once every 5 minutes rather than 15 minutes, or with each determination of the glucose level). In this manner, to the extent that adjustment to the insulin delivery rate is desirable, the frequency of the adjustment may be associated with the monitored glucose level such that, for example, control unit 140 may be configured to determine, with each received glucose value, whether adjustment to the insulin delivery rate is needed.

Figure 8:
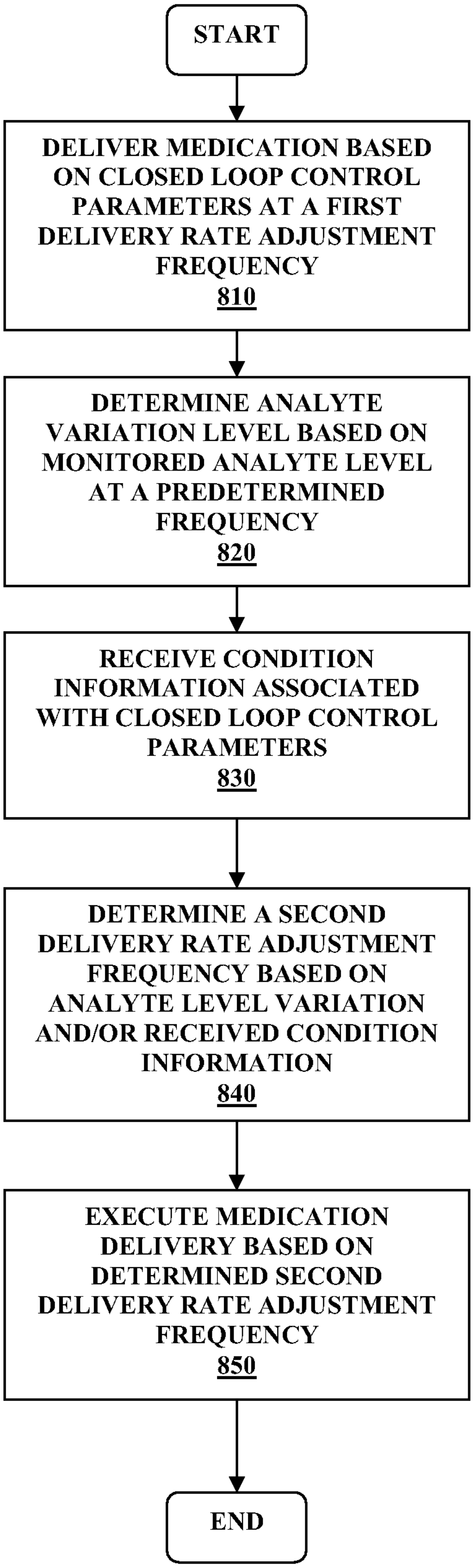
FIG. 8 is a flowchart illustrating variable rate control in a closed loop control system in accordance with another embodiment of the present disclosure.

FIG. 8 is a flowchart illustrating variable rate control in a closed loop control system in accordance with another embodiment of the present disclosure. Referring to FIGS. 1 and 8, control unit 140 (FIG. 1) in one aspect may be configured to instruct the delivery unit 120 (FIG. 1) to deliver medication based on closed loop control parameters at a first delivery rate adjustment frequency (810). Thereafter, the analyte variation level is determined based on the monitored analyte level at a predetermined frequency (820). Referring back to FIG. 8, one or more condition information (for example, but not limited to an anticipated meal event) associated with the closed loop control parameters is received (830). Thereafter, a second delivery rate adjustment frequency is determined based on the analyte level variation and/or received condition information (840), and the medication delivery is executed (for example, by the insulin delivery unit 120 (FIG. 1)) at the determined second delivery rate adjustment frequency (850).

In this manner, in one aspect, control unit 140 is configured to maximize responsiveness to substantial variation in monitored glucose level, or in anticipation of variation in glucose level, while providing lower power requirements for the various components of the system 100 (FIG. 1). Within the scope of the present disclosure, other suitable time intervals or frequency may be used for the glucose monitoring, and further, the associated adjustment to the insulin delivery rate.

That is, embodiments of the present disclosure allow for lower rate of control commands, for example, where the delivery unit 120 and the analyte monitoring unit 130 are configured in the system 100 as separate components, with the control unit 140 provided with the analyte monitoring unit 130 and communicating wirelessly with the delivery unit 120, and each being powered by a respective power supply such as a battery.

Figure 9:
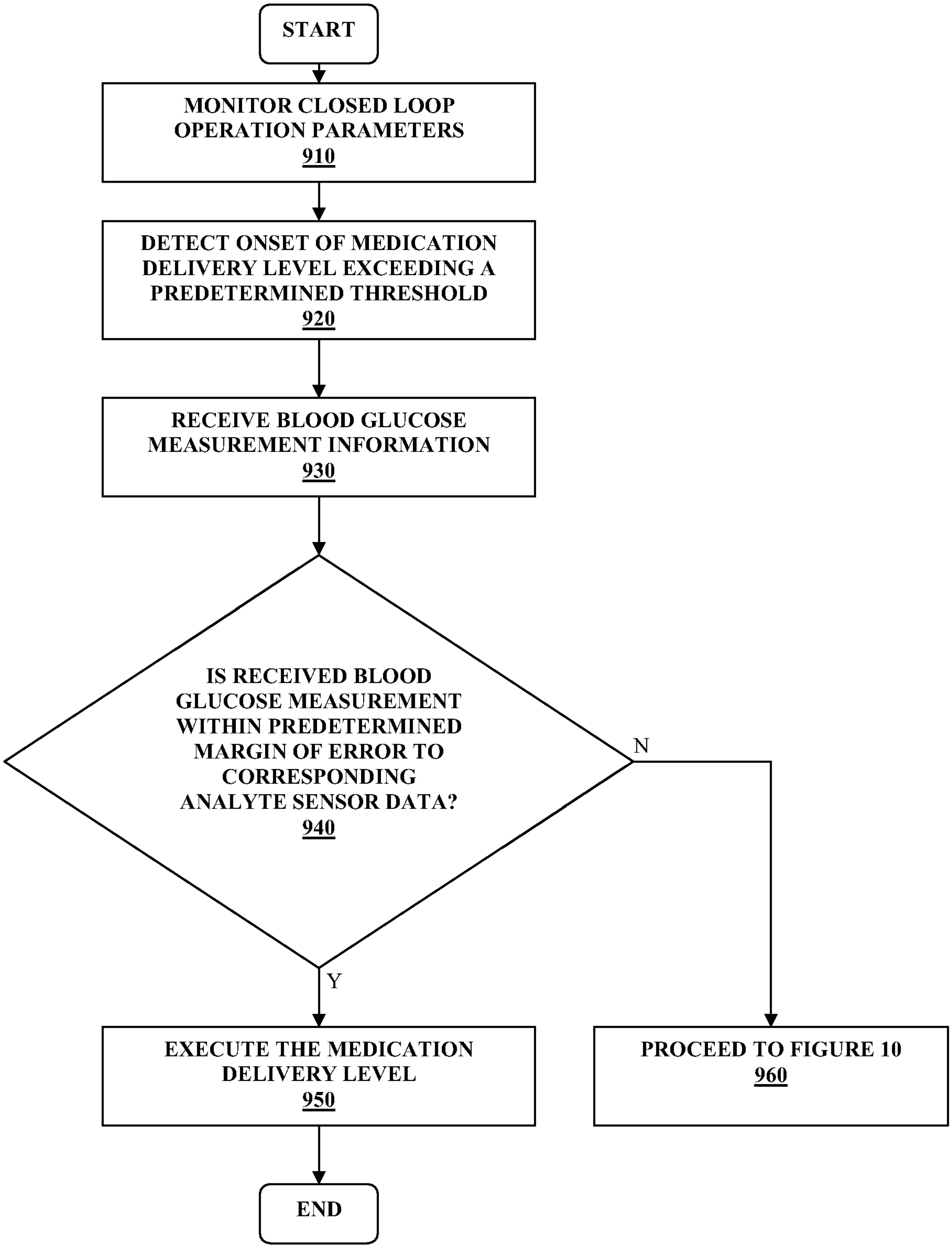
FIGS. 9-10 are flowcharts illustrating blood glucose measurement to improve accuracy of the closed loop control system in accordance with another embodiment of the present disclosure.
Figure 10:
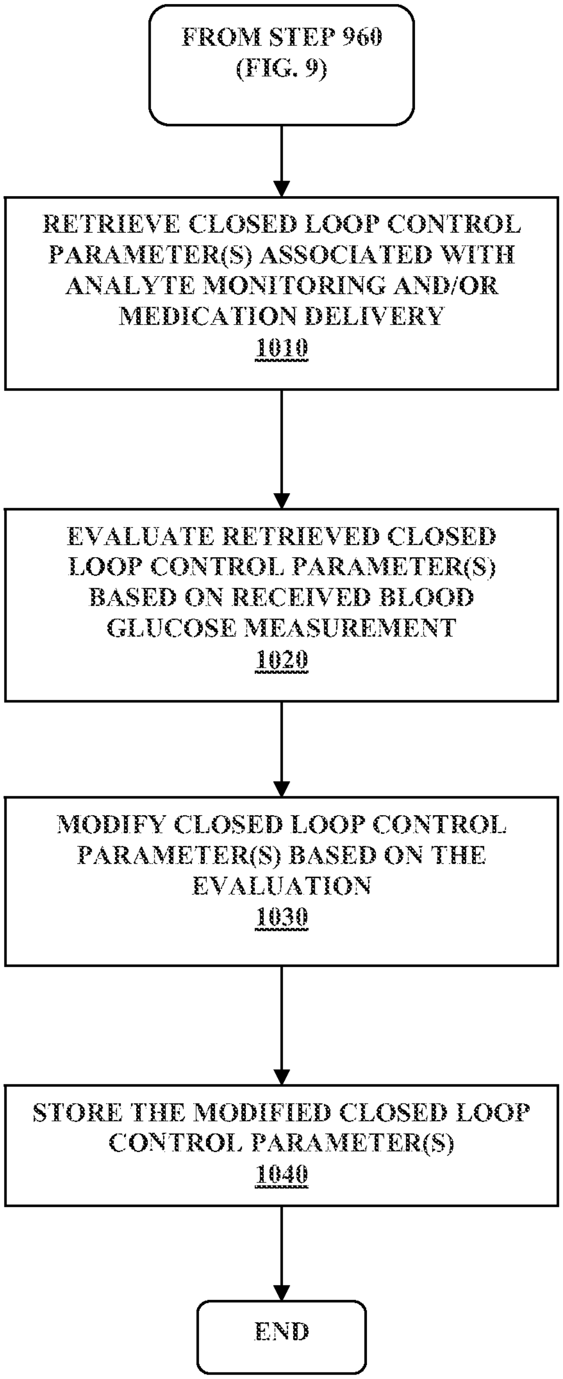

FIGS. 9-10 are flowcharts illustrating blood glucose measurement to improve accuracy of the closed loop control system in accordance with another embodiment of the present disclosure. Referring to FIGS. 1, 9 and 10, closed loop operation parameters are monitored (910) and when onset of medication delivery level (for example, a large insulin dosage level) that exceeds a predetermined threshold level is detected (920) a blood glucose measurement information is received (930) (for example, from a blood glucose meter or manually entered by user input). Based on the received blood glucose measurement information, it is determined whether the received blood glucose measurement is within a predetermined margin of error to a time corresponding analyte sensor data (940). In other words, it is determined whether the sensor data correlates to the blood glucose measurement within a predetermined margin of error.

Referring back to FIG. 9, if it is determined that the analyte sensor data and the blood glucose measurement are within the predetermined margin of error, then the detected onset of medication delivery level is maintained and the delivery unit 120 delivers that level of medication (950). On the other hand, if it is determined that the blood glucose measurement received is not within the predetermined margin of error (940), then referring back to FIG. 10 (960), the closed loop control parameters associated with the analyte monitoring and/or the medication delivery are retrieved (1010), and the retrieved closed loop control parameters are evaluated based on the received blood glucose measurement (1020).

For example, one or more of the closed loop control parameters retrieved may include a request for an additional blood glucose measurement value, an instruction to modify or adjust insulin delivery rate, command to disable closed loop control operation and initiate semi-closed loop control operation or manual control operation, or instruction to recalibrate the analyte sensor, among others. Referring back to FIG. 10, upon evaluation of the retrieved one or more closed loop control parameters, the retrieved one or more parameters may be modified (1030) and thereafter the modified one or more closed loop control parameters is stored (1040).

In this manner, for example, under the control of the control unit 140 (FIG. 1) executing the closed loop control algorithm, when it is detected that a large amount of insulin is to be delivered by the delivery unit 120, the control unit 140, as a safety measure, for example, may prompt the user to enter a current blood glucose measurement (for example, using an in vitro blood glucose meter), to confirm and/or verify the accuracy of the analyte sensor level from the analyte monitoring unit 130 based on which the large amount of insulin to be delivered was determined for execution. For example, a Kalman filter may be used as part of the control unit 140 to process the analyte sensor data and the received blood glucose measurement to optimally adjust the insulin level.

In one aspect, the request or prompt to enter the blood glucose measurement may be initiated when the determined insulin amount for delivery in the closed loop control system 100 exceeds a predetermined safety level established, for example, by a healthcare provider or physician, where the safety level includes, for example, the highest insulin delivery rate without blood glucose measurement confirmation. Within the scope of the present disclosure, other conditions or parameters may be used to trigger the request for blood glucose measurement for confirming sensor accuracy, glucose level verification, and the like.

Further, in another aspect, the control unit 140 may be configured to discontinue requesting blood glucose measurements (even when the insulin level to be delivered exceeds the predetermined safety level) when a predetermined number of successful blood glucose measurement confirmations have occurred and the analyte sensor is considered accurate and stable. Still another aspect of the present disclosure includes modifying the safety level for the highest rate of insulin delivery based on the determination of sensor stability and accuracy in view of, for example, successive confirmation of blood glucose measurements to the corresponding sensor values.

Figure 11:
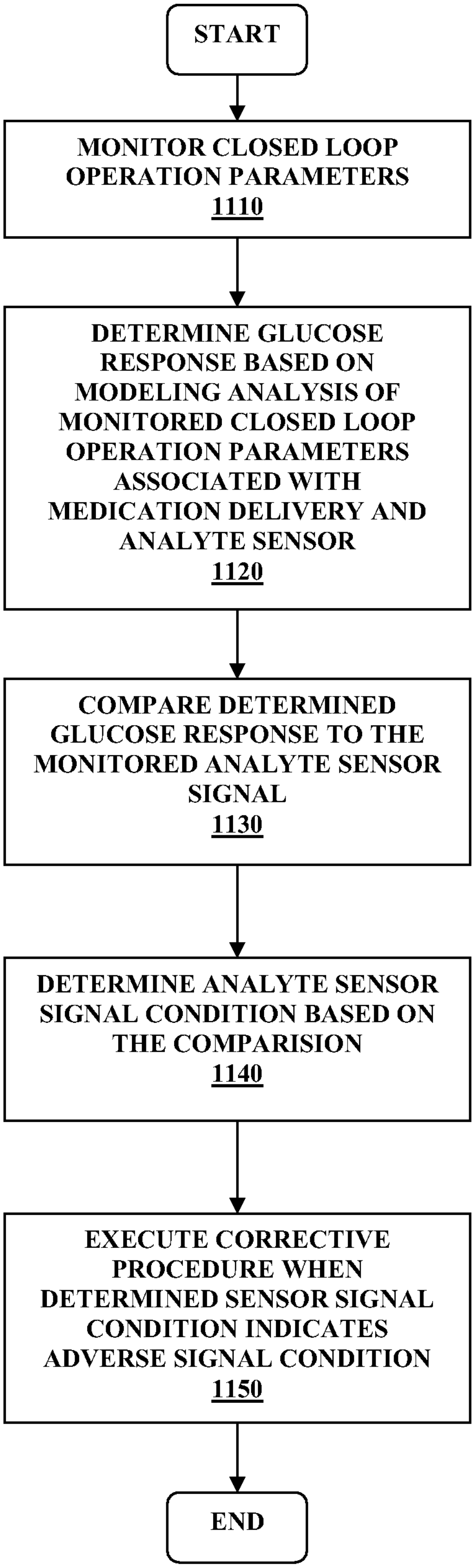
FIG. 11 is a flowchart illustrating medication delivery information to determine analyte sensor condition in a closed loop control system in accordance with one embodiment of the present disclosure.

FIG. 11 is a flowchart illustrating medication delivery information to determine analyte sensor condition in a closed loop control system in accordance with one embodiment of the present disclosure. Referring to FIGS. 1 and 11, in the closed loop control operation state of the closed loop control system 100, control unit 140 (FIG. 1) in one aspect monitors closed loop operation parameters (1110) and performs a predictive modeling analysis of the monitored closed loop control operation parameters associated with the medication delivery and analyte sensor to determine a predictive glucose response (1120). Thereafter, the determined predictive glucose response is compared with the corresponding monitored analyte sensor signal (1130) and a sensor signal condition based on the comparison is determined (1140). For example, based on the comparison, the sensor signal condition may indicate a signal attenuation condition of the glucose sensor. Referring back to FIG. 11, when the sensor signal condition indicates an adverse signal condition or a condition associated with a corrective action or procedure, the corresponding corrective procedure is retrieved and executed by the control unit 140 (1150).

In this manner, in one aspect, using the insulin delivery information, and based on a predictive model implemented to determine a modeled glucose sensor signal, the robustness of the closed loop control system 100 may be enhanced and accuracy of the overall system 100 improved. In one aspect, the predictive model used may include a routine or algorithm that describes glucose response or behavior based on one or more exogenous factors including, among others, insulin delivery information, meal intake, exercise events, and the like, as well as prior monitored sensor data. Accordingly, in one aspect, real time insulin delivery information may be used to improve glucose sensor anomalies such as signal dropouts and early signal attenuation.

For example, as discussed above, the generated modeled glucose sensor response is compared in one aspect to the actual measured sensor data, and based on the comparison, it may be determined that anomalies exist with the glucose sensor. For example, control unit 140 may determine, based on the comparison that sensor signal dropout or early signal attenuation is detected, and thus may prompt the user to enter a reference blood glucose measurement value. In addition, certain alarm or notification functions related to the monitored analyte level such as hypoglycemic alarm, output display of glucose values in real time, may be modified or disabled given the detected anomaly with the sensor signal.

In one aspect, other variables may be compared based on the predictive model and the actual measured sensor signal such as, for example, rate of change of the glucose level determined based on the actual measured values from the sensor and compared with the modeled rate of change information. Additionally, upon determination of the sensor signal drop out or early signal attenuation condition, operations of the analyte monitoring unit 130 may be adjusted accordingly, for example, to mitigate or address the signal abnormality. For example, when such sensor signal condition indicates adverse signal condition at the time of scheduled sensor calibration, the calibration attempt may be disqualified and the user may be instructed to perform another calibration or to delay the calibration until the sensor signal has stabilized and the indicated adverse signal condition is no longer present.

Figure 12:
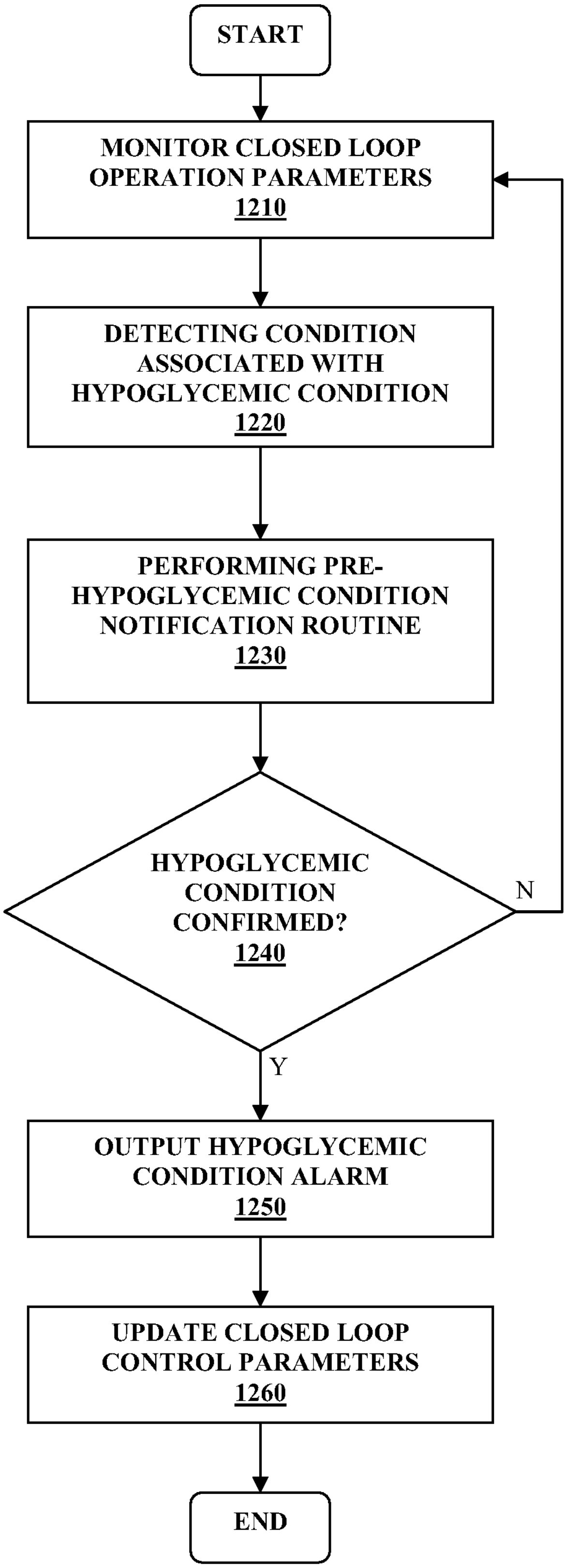
FIG. 12 is a flowchart illustrating detection of false hypoglycemic alarm condition in a closed loop control system in accordance with one embodiment of the present disclosure.

FIG. 12 is a flowchart illustrating detection of false hypoglycemic alarm condition in a closed loop control system in accordance with one embodiment of the present disclosure. Referring to FIGS. 1 and 12, in one aspect, condition associated with hypoglycemic state is detected (1220) based on monitored closed loop operation parameters (1210) by, for example, the control unit 140 (FIG. 1). Upon detection of the condition associated with the hypoglycemic state, a pre-hypoglycemic condition notification routine is performed (1230). If the hypoglycemic state or condition is confirmed (1240), then a corresponding notification such as a hypoglycemic alarm is output (1250), and the closed loop control parameters are accordingly updated to take into account of the detected hypoglycemic condition (1260).

On the other hand, if the hypoglycemic condition is not confirmed (1240), then the routine returns to monitor the closed loop operation parameters (1210). That is, in one aspect, when a condition associated with hypoglycemia is detected, the control unit 140 may be configured to confirm the presence of the detected hypoglycemic state before asserting an alarm notification, for example, to the user. In this manner, potential false hypoglycemic alarms are minimized based on, for example, presence of glucose sensor signal dropout or early signal attenuation or other sensor anomaly state that indicates a false low glucose level.

For example, in accordance with the embodiments of the present disclosure, hypoglycemic alarms or notifications are provided with sensor signal dropout tolerance levels. More specifically, based on the medication delivery rate information, and other parameters associated with the closed loop control operation, the control unit 140 may be configured to determine a degree or level of uncertainly in the measured sensor signal based on the predicted or anticipated glucose level derived, for example, based on the parameters associated with the closed loop control algorithm, including, such as amount of insulin delivered, insulin on board information, glucose rate of change information, among others.

In one aspect, when the onset of a potential hypoglycemic condition is detected, the control unit 140 may be configured to confirm the presence of the hypoglycemic condition, by for example, requiring additional sensor data to be received and analyzed and determining that the sensor signals indicate a persistent low glucose value. In this manner, the rather than asserting the hypoglycemic condition notification immediately upon detection of a sensor signal level below the alarm threshold, control unit 140 in one aspect is configured to confirm the presence of the hypoglycemic condition, and upon confirmation, to assert the alarm or notification associated with the hypoglycemic condition.

In another aspect, upon detection of a potential hypoglycemic condition, control unit 140 may be configured to initiate and execute a sensor signal dropout detection algorithm to determine whether the detected potential hypoglycemic condition is associated with sensor signal dropout or attributable to low glucose level. Moreover, in a further aspect, upon detection of the potential hypoglycemic condition, control unit 140 may be configured to assert an alert notification (associated with less urgency or criticality), and if the potential hypoglycemic condition is confirmed, to assert the hypoglycemic condition alarm. For example, the alert notification may include a single audible beep that does not repeat. If the glucose is persistently below the hypoglycemic threshold (or alarm condition level), or below a lower safety threshold, the notification may be escalated to an alarm, for example, with three consecutive audible beeps with or without repeat routines. In this manner, for example, if the sensor signal dropout occurs during night time when the user is asleep, the alert notification may not be loud enough to wake the user, but may be sufficient to cause the user to move or roll over in bed, for example, resulting in the sensor dropout condition being no longer present.

In the manner described, in accordance with the various embodiments of the present disclosure, a robust closed loop control system is provided that includes safety checks and verifications to address potential errors and/or anomalies in detected or monitored conditions and/or parameters enhancing the accuracy and confidence level of the closed loop control operation in the treatment of diabetic conditions.

A method in accordance with one embodiment may include monitoring a plurality of parameters associated with a closed loop control operation including continuously monitoring a physiological condition and automatic administration of a medication, detecting a signal level associated with the monitored physiological condition deviating from a predetermined threshold level, retrieving the medication level administered associated with a time period of the detected signal level, applying the retrieved medication level to the detected signal based on a predefined predictive model to generate a predictive signal, and comparing the detected signal to the predictive signal to determine whether a condition associated with the detected signal level is present.

The signal level may be associated with an analyte level and the condition associated with the detected signal level includes early signal attenuation condition.

A method in accordance with another embodiment includes monitoring control parameters in a closed loop control operation including continuously monitoring a physiological condition and automatic administration of a medication, determining glucose response level based on a predictive model including a delivery rate of the administered medication, comparing the determined glucose response level to a time corresponding analyte sensor signal based on the monitored physiological condition to determine a sensor signal condition, and executing a corrective procedure when the determined sensor signal condition based on the comparison indicates an adverse signal condition.

The adverse signal condition may include a signal attenuation level below a predetermined level.

The method may include confirming the existence of the adverse signal condition prior to executing the corrective procedure, where the adverse signal condition may be associated with an impending hypoglycemic condition.

In another aspect, the method may include asserting a notification associated with the adverse signal condition, where the notification may include one or more of an audible alarm, a vibratory alarm, a visual alarm, or one or more combinations thereof.

The corrective procedure may include calibration of the analyte sensor.

In one aspect, executing the corrective procedure may include waiting a predetermined time period to confirm the presence of the adverse signal condition prior to executing the corrective procedure.

The predictive model may include a predictive algorithm for modeling a glycemic condition.

A device in accordance with another embodiment includes one or more processors, and a memory operatively coupled to the one or more processors, the memory for storing instructions which, when executed by the one or more processors, causes the one or more processors to monitor control parameters in a closed loop control operation including continuously monitoring a physiological condition and automatic administration of a medication, determine glucose response level based on a predictive model including a delivery rate of the administered medication, compare the determined glucose response level to a time corresponding analyte sensor signal based on the monitored physiological condition to determine a sensor signal condition, and execute a corrective procedure when the determined sensor signal condition based on the comparison indicates an adverse signal condition.

The adverse signal condition may include a signal attenuation level below a predetermined level.

The memory for storing instructions which, when executed by the one or more processors, may cause the one or more processors to confirm the existence of the adverse signal condition prior to executing the corrective procedure.

The adverse signal condition may be associated with an impending hypoglycemic condition.

The memory for storing instructions which, when executed by the one or more processors, may cause the one or more processors to assert a notification associated with the adverse signal condition, where the notification may include one or more of an audible alarm, a vibratory alarm, a visual alarm, or one or more combinations thereof.

In a further aspect, the corrective procedure may include calibration of the analyte sensor.

The memory for storing instructions which, when executed by the one or more processors, may cause the one or more processors to wait a predetermined time period to confirm the presence of the adverse signal condition prior to executing the corrective procedure.

The predictive model in a further aspect may include a predictive algorithm for modeling a glycemic condition.

What is claimed is:

1. A method for controlling delivery of insulin, the method comprising:

- monitoring one or more parameters associated with delivery of insulin according to a control algorithm, wherein the one or more parameters include a monitored glucose level;
- detecting a signal level associated with the monitored glucose level;
- detecting an adverse signal condition based on the one or more parameters; and
- executing a corrective action based on the detection of the adverse signal condition, wherein the corrective action comprises outputting a prompt for entry of a blood glucose measurement on a user interface.

2. The method of claim 1, wherein the adverse signal condition comprises signal dropout or signal attenuation.

3. The method of claim 1, wherein the adverse signal condition is associated with an impending hypoglycemic condition.

4. The method of claim 1, further comprising detecting the adverse signal condition based on a predictive model.

5. The method of claim 4, further comprising determining a predictive glucose response level based on the predictive model, and wherein the detection of the adverse signal condition is based on a comparison of the predictive glucose response level to the monitored glucose level.

6. The method of claim 1, wherein the corrective action further comprises modifying a glucose level alarm.

7. The method of claim 1, wherein the corrective action further comprises disabling a glucose level alarm.

8. The method of claim 1, wherein the corrective action further comprises instructing the user to delay a calibration for a period of time.

9. The method of claim 1, further comprising issuing a notification associated with the adverse signal condition.

10. The method of claim 1, wherein the control algorithm comprises a closed loop control algorithm.

11. The method of claim 1, wherein the adverse signal condition comprises an insulin delivery amount exceeding an insulin delivery threshold.

12. A system for controlling delivery of insulin, comprising:

- a medication delivery device configured to administer insulin according to a control algorithm;
- a processor in communication with the medication delivery device; and
- a memory coupled to the processor and storing instructions that, when executed by the processor, cause the processor to:
  - monitor one or more parameters associated with delivery of insulin according to the control algorithm, wherein the one or more parameters include a monitored glucose level;
  - detect a signal level associated with the monitored glucose level;
  - detect an adverse signal condition based on the one or more parameters; and
  - execute a corrective action based on the detection of the adverse signal condition, wherein the corrective action comprises outputting a prompt for entry of a blood glucose measurement on a user interface.

13. The system of claim 12, wherein the adverse signal condition comprises signal dropout or signal attenuation.

14. The system of claim 12, wherein the processor is further caused to determine a predictive glucose response level based on a predictive model, and wherein detection of the adverse signal condition is based on a comparison of the predictive glucose response level to the monitored glucose level.

15. The system of claim 12, wherein the control algorithm comprises a closed loop control algorithm.

16. The system of claim 12, wherein the corrective action further comprises one or more of prompting the user to enter a blood glucose measurement, modifying a glucose level alarm, disabling a glucose level alarm, or instructing the user to delay a calibration for a period of time.

17. The system of claim 12, wherein the medication delivery device comprises the processor.

18. The system of claim 12, further comprising a data processing device comprising a display, wherein the data processing device is in wireless communication with the medication delivery device, and wherein the data processing device comprises the processor.

19. The system of claim 12, wherein the medication delivery device comprises an external infusion pump or an on-body patch pump.

20. A non-transitory computer-readable medium having instructions stored thereon that, when executed by at least one computing device, cause the at least one computing device to perform operations comprising:

- monitor one or more parameters associated with delivery of insulin according to a control algorithm, wherein the one or more parameters include a monitored glucose level;
- detect a signal level associated with the monitored glucose level;
- detect an adverse signal condition based on the one or more parameters; and
- execute a corrective action based on the detection of the adverse signal condition,
- wherein the corrective action comprises outputting a prompt for entry of a blood glucose measurement.

* * * * *